(12) United States Patent
Galdonik et al.

(10) Patent No.: US 9,186,237 B2
(45) Date of Patent: Nov. 17, 2015

(54) EMBOLIC PROTECTION DURING PERCUTANEOUS HEART VALVE REPLACEMENT AND SIMILAR PROCEDURES

(75) Inventors: Jason A. Galdonik, Hanover, MN (US); Matthew F. Ogle, Fitchburg, WI (US); Edward Anderson, Maple Grove, MN (US); Mark W. I. Webster, Auckland (NZ)

(73) Assignee: Lumen Biomedical, Inc., Maple Grove, MN (US)

( * ) Notice: Subject to any disclaimer, the term of this patent is extended or adjusted under 35 U.S.C. 154(b) by 737 days.

(21) Appl. No.: 13/398,577

(22) Filed: Feb. 16, 2012

(65) Prior Publication Data

US 2012/0150211 A1    Jun. 14, 2012

Related U.S. Application Data

(63) Continuation of application No. 13/218,183, filed on Aug. 25, 2011, now Pat. No. 8,382,788, which is a continuation of application No. 12/489,108, filed on Jun. 22, 2009, now Pat. No. 8,206,412.

(60) Provisional application No. 61/132,823, filed on Jun. 23, 2008.

(51) Int. Cl.
*A61F 2/01* (2006.01)

(52) U.S. Cl.
CPC . *A61F 2/01* (2013.01); *A61F 2/013* (2013.01); *A61F 2002/011* (2013.01);
(Continued)

(58) Field of Classification Search
CPC .................... A61F 2002/011; A61F 2002/018; A61F 2230/0006; A61F 2230/0065; A61F 2230/0067; A61F 2/01; A61F 2/013

USPC .......... 604/8, 9; 606/108, 191, 194, 198, 200; 623/2.11
See application file for complete search history.

(56) References Cited

U.S. PATENT DOCUMENTS

| | | | |
|---|---|---|---|
| 5,200,248 A | 4/1993 | Thompson et al. | |
| 6,051,014 A | 4/2000 | Jang | |

(Continued)

FOREIGN PATENT DOCUMENTS

| | | |
|---|---|---|
| JP | 2003-505216 A | 2/2003 |
| JP | 2003-526451 A | 9/2003 |

(Continued)

OTHER PUBLICATIONS

Offic Action for co-pending Japanese application 2011-516280, dated Jun. 10, 2014 (4 pages with translation).

(Continued)

*Primary Examiner* — Ashley Fishback
(74) *Attorney, Agent, or Firm* — Dardi & Herbert, PLLC; Peter S. Dardi; Kayla J. Fossen

(57) ABSTRACT

Various devices are described to provide filtering of flow from the aorta to the left carotid artery and the right carotid artery. The filters can be brought into a desired position through one or more peripheral arteries. A single filter device can provide the desired filtering or a plurality of devices can be used. In particular a single filter device can span between the brachiocephalic artery and the left carotid artery. These filter devices can be used effectively to capture emboli generated during procedures on the heart so that emboli do not travel to the patient's brain where the emboli can cause a stroke or other adverse event. In particular, these filters can be used during percutaneous procedures on the heart, such as endovascular heart valve replacement.

20 Claims, 16 Drawing Sheets

(52) U.S. Cl.
CPC .. *A61F 2002/018* (2013.01); *A61F 2230/0006* (2013.01); *A61F 2230/008* (2013.01); *A61F 2230/0065* (2013.01); *A61F 2230/0067* (2013.01); *A61F 2230/0069* (2013.01); *A61F 2230/0093* (2013.01)

(56) References Cited

U.S. PATENT DOCUMENTS

| | | | |
|---|---|---|---|
| 6,126,673 | A | 10/2000 | Kim et al. |
| 6,146,396 | A | 11/2000 | Konya et al. |
| 6,287,321 | B1 | 9/2001 | Jang |
| 6,336,934 | B1 | 1/2002 | Gilson et al. |
| 6,454,799 | B1 | 9/2002 | Schreck |
| 6,499,487 | B1 | 12/2002 | McKenzie et al. |
| 6,517,559 | B1 | 2/2003 | O'Connell |
| 6,537,297 | B2 | 3/2003 | Tsugita et al. |
| 6,663,652 | B2 | 12/2003 | Daniel et al. |
| 6,719,717 | B1 | 4/2004 | Johnson et al. |
| 6,726,621 | B2 | 4/2004 | Suon et al. |
| 6,740,061 | B1 | 5/2004 | Oslund et al. |
| 6,958,074 | B2 | 10/2005 | Russell |
| 7,303,575 | B2 | 12/2007 | Ogle |
| 7,329,278 | B2 | 2/2008 | Seguin et al. |
| 8,021,351 | B2 | 9/2011 | Boldenow et al. |
| 8,092,483 | B2 | 1/2012 | Galdonik et al. |
| 2002/0022858 | A1 | 2/2002 | Demond et al. |
| 2002/0068015 | A1 | 6/2002 | Polaschegg et al. |
| 2002/0165573 | A1 | 11/2002 | Barbut |
| 2003/0144686 | A1 | 7/2003 | Martinez et al. |
| 2004/0002730 | A1 | 1/2004 | Denison et al. |
| 2004/0006370 | A1* | 1/2004 | Tsugita ................. 606/200 |
| 2004/0243175 | A1 | 12/2004 | Don Michael |
| 2005/0085847 | A1 | 4/2005 | Galdonik et al. |
| 2005/0137696 | A1 | 6/2005 | Salahieh et al. |
| 2005/0209631 | A1 | 9/2005 | Galdonik et al. |
| 2005/0277976 | A1 | 12/2005 | Galdonik et al. |
| 2006/0047301 | A1 | 3/2006 | Ogle |
| 2006/0161241 | A1 | 7/2006 | Barbut et al. |
| 2006/0200047 | A1 | 9/2006 | Galdonik et al. |
| 2007/0038226 | A1 | 2/2007 | Galdonik et al. |
| 2007/0060944 | A1 | 3/2007 | Boldenow et al. |
| 2007/0208302 | A1 | 9/2007 | Webster et al. |
| 2008/0033467 | A1 | 2/2008 | Miyamoto et al. |
| 2008/0065145 | A1 | 3/2008 | Carpenter |
| 2008/0086110 | A1 | 4/2008 | Galdonik et al. |
| 2008/0109088 | A1 | 5/2008 | Galdonik et al. |
| 2008/0172066 | A9 | 7/2008 | Galdonik et al. |
| 2010/0010476 | A1 | 1/2010 | Galdonik et al. |
| 2010/0179583 | A1 | 7/2010 | Carpenter et al. |
| 2010/0179584 | A1 | 7/2010 | Carpenter et al. |
| 2010/0179585 | A1 | 7/2010 | Carpenter et al. |
| 2010/0179647 | A1 | 7/2010 | Carpenter et al. |
| 2010/0185231 | A1 | 7/2010 | Lashinski |
| 2010/0191276 | A1 | 7/2010 | Lashinski |
| 2010/0211095 | A1 | 8/2010 | Carpenter |
| 2010/0324589 | A1 | 12/2010 | Carpenter et al. |
| 2011/0022076 | A1 | 1/2011 | Lashinski |

FOREIGN PATENT DOCUMENTS

| | | |
|---|---|---|
| JP | 2003-290231 A | 10/2003 |
| JP | 3535098 B2 | 6/2004 |
| JP | 2006-500187 A | 1/2006 |
| JP | 2008-511401 A | 4/2008 |
| JP | 2008-515463 A | 5/2008 |
| WO | 01/67989 A2 | 9/2001 |
| WO | 2004/026175 A1 | 4/2004 |
| WO | 2005/118050 A2 | 12/2005 |
| WO | 2006/026371 A1 | 3/2006 |
| WO | 2008033845 A2 | 3/2008 |
| WO | 2010081025 A1 | 7/2010 |
| WO | 2010083527 A2 | 7/2010 |
| WO | 2010088520 A2 | 8/2010 |
| WO | 2011017103 A2 | 2/2011 |
| WO | 2011034718 A2 | 3/2011 |

OTHER PUBLICATIONS

Search Report for corresponding European Patent Application No. 09798236.7, mailed Jul. 20, 2012.
Fiber Innovation Technology: 4DG Fibers: http://web.archive.org/web/2011030070010/http://fitfibers.com/4DG_Fibers.htm; (Oct. 30, 2001).
Fiber Innovative Technology: biocomponent and specialty fibers; FIT Capabilities; http://web.archive.org/web/20010217040848/http://www.fitfibers.com/capablities.htm (Feb. 17, 2001).
Fiber Innovative Technology: biocomponent and specialty fibers; FIT Products; http://web.archive.org/web/20010408003529/http://www.fitfibers.com/product.htm.
U.S. Appl. No. 61/145,149, filed Jan. 16, 2009 entitled "Intravascular Blood Filter" by Randall Lashinski—29 pages.
U.S. Appl. No. 61/148,054, filed Jan. 16, 2009 entitled "Illuminated Intravascular Blood Filter" by Randall Lashinski—41 pages.
U.S. Appl. No. 61/228,703, filed Jul. 27, 2009 entitled "Dual Endovascular Filter and Methods of Use" by Randall Lashinski—20 pages.
Office Action for co-pending Japanes application 2011-516280, dated Aug. 20, 2013 (9 pages with translation).

* cited by examiner

EMBOLIC PROTECTION DURING PERCUTANEOUS HEART VALVE REPLACEMENT AND SIMILAR PROCEDURES

CROSS REFERENCE TO RELATED APPLICATIONS

The present application is a continuation of U.S. patent application Ser. No. 13/218,183 filed Aug. 25, 2011, now U.S. Pat. No. 8,382,788 entitled "Embolic Protection During Percutaneous Heart Valve Replacement and Similar Procedures", incorporated herein by reference, which is a continuation of U.S. patent application Ser. No. 12/489,108 filed Jun. 22, 2009, now U.S. Pat. No. 8,206,412 entitled "Embolic Protection During Percutaneous Heart Valve Replacement and Similar Procedures", incorporated herein by reference, which claims priority to U.S. provisional patent application Ser. No. 61/132,823 to Galdonik et al. filed on Jun. 23, 2008, entitled "Embolic Protection During Percutaneous Heart Valve Replacement and Similar Procedures", incorporated herein by reference.

FIELD OF THE INVENTION

The inventions, in general, are related to embolic protection devices placed in blood vessels during surgical intervention and corresponding methods. The inventions are further related to embolic filters placed in blood vessels during percutaneous heart valve replacement, as well as corresponding methods. The devices and methods can be directed to the prevention of the flow of emboli into the carotid arteries.

BACKGROUND

Less invasive procedures can provide desirable medical results with reduced recovery time and reduced risk to the patient. Thus, many surgical procedures are performed using endoscopes or the like in percutaneous formats. A large number of less invasive procedures within the cardiovascular system are now commonly performed, such as angiograms, angioplasty procedures and stent delivery procedures.

Heart valve prostheses have been successfully used to replace damaged natural heart valves that no longer perform their functions in a satisfactory way. Commercial heart valve prostheses include both mechanical valves with rigid occluders and tissue-based prostheses with flexible leaflets. These valves have been implanted surgically through the chest with the patient on cardiopulmonary bypass.

SUMMARY OF THE INVENTION

In a first aspect, the invention pertains to a method for providing embolic protection comprising placing separate protective devices to inhibit emboli migration into the left common carotid artery and the right common carotid artery. The devices can be associated with independent delivery devices or on a common delivery device. One or both of the devices comprises a filter, and one of the devices can be an occlusive device. In some embodiments, the filter comprises fibers that form a filtration matrix upon deployment. The device inhibiting migration of emboli into the right common carotid artery can be within the right common carotid artery or within the brachiocephalic artery. An aspiration catheter can be used to facilitate recovery of one or both of the devices. In some embodiments, one or both of the devices may be un-tethered. The devices can be deployed prior to performing a percutaneous valve replacement procedure, and the device can be removed following completion of the procedure to replace a heart valve using a percutaneous procedure.

In a second aspect, the invention pertains to a method for providing embolic protection during endovascular procedures on a patient's heart. The method can comprise positioning one or more vascular filter elements to filter flow into the right carotid artery, such as the right common carotid artery or the right interior carotid artery, and the left carotid artery, such as the left common carotid artery or the left interior carotid artery. Generally, each of the one or more vascular filter elements are delivered through the right subclavian artery, the left subclavian artery, or a combination thereof.

In a further aspect, the invention pertains to a filtration system comprising a catheter and a filter device. The catheter generally comprises a tubular element having a proximal end and a distal end, a lumen extending through the tubular element, and an expandable structure mounted toward the distal end on the exterior of the catheter. The filter device generally comprises a guide structure and a filter element mounted on the guide structure, in which the lumen of the catheter is suitable for the delivery of filter element mounted of the guide structure.

In another aspect, the invention pertains to a filtration system comprising a catheter, a first filter device and a second filter device. The catheter generally comprises a tubular element with a proximal end and a distal end, and a lumen extending through the tubular element. The first filter device generally comprises a first guide structure and a first filtration element attached to the first guide structure, and the second filter device generally comprises a second guide structure and a second filtration element attached to the second guide structure. The catheter can have one or more lumens suitable for the delivery of the first filter device and the second filter device. Also, the catheter can comprises a first port configured such that the first filter device can exit the catheter through the first port and a second port configured such that the second filter device can exit through the second port at an angled direction relative to the first filter device exiting the first port.

In other aspects, the invention pertains to a filter device comprising an overtube, a first corewire, a second corewire, a first filter element having a delivery configuration and a deployed configuration, and a second filter element having a delivery configuration and a deployed configuration, the first filter element being positioned distal to the second filter element. Generally, at least a portion of the first corewire and at least a portion of the second corewire are within the overtube. The configuration of the first filter element can be controlled through the relative position of the first corewire and the overtube, and the configuration of the second filter element can be controlled through the relative position of the second corewire and the overtube.

In additional aspects, the invention pertains to a filtration system comprising a first sealing member, a second sealing member, a lumen extending through the interior of each sealing member, and one or more filtration elements associated with the lumen. The first sealing member and the second sealing member can each have a configuration extending outward. The filtration elements can be configured such that flow through the lumen extending past the first sealing member and the second sealing member passes through the one or more filtration elements.

Furthermore, the invention pertains to a method for the endovascular replacement of a heart valve. The method comprises positioning one or more filter elements to filter flow from the heart flowing into the right carotid artery and the left carotid artery, and delivering a heart valve delivery catheter through the descending aorta or the subclavian artery to the heart to effect at least a step related to removal of a heart valve or the placement of a prosthetic heart valve.

DETAILED DESCRIPTION OF PREFERRED EMBODIMENTS

Figure 1:
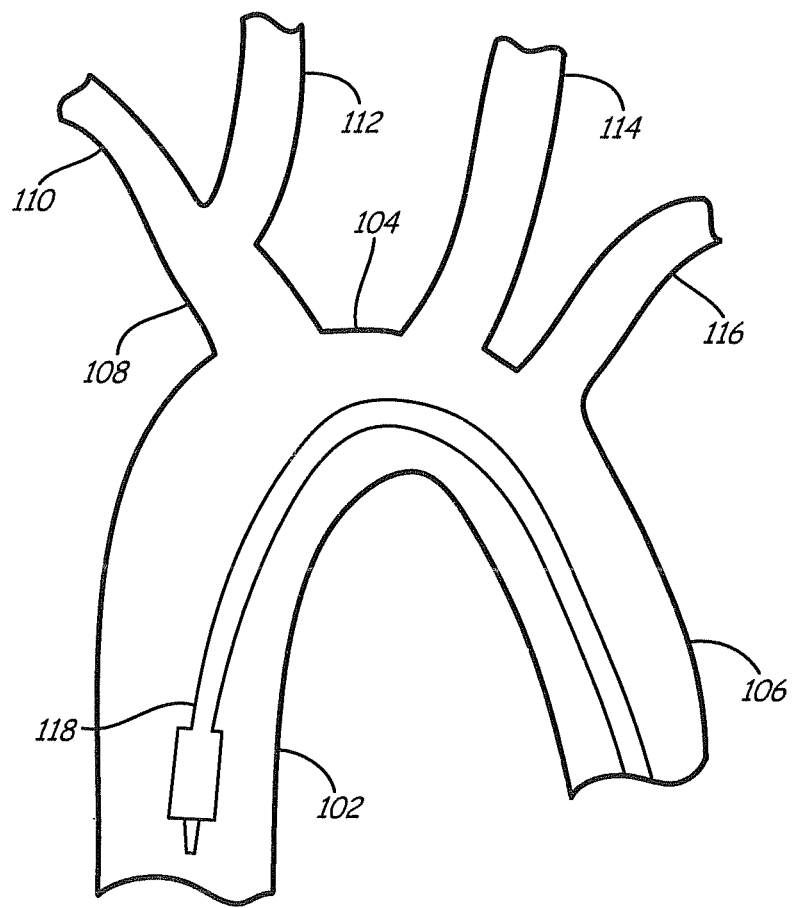
FIG. 1 is a sectional view of the aortic arch and major branching arteries.

Devices and corresponding procedures are described herein that can capture emboli generated in procedures involving the heart, and in particular the left chambers of the heart, to reduce or eliminate release of emboli into selected arteries, e.g., the carotid arteries. It may be desirable to perform procedures on the heart using less invasive techniques that approach the heart through the blood vessels such that open heart surgery may not be needed. Any debris created in the vicinity of the heart that flows into the aorta can flow into the carotid arteries where the emboli can cause a stroke or other undesirable outcome. In general, the filter system can be delivered independent of the heart treatment structures, such that the filters can be put into place at a desirable time, such as prior to events that can generate emboli. In some embodiments, portions of the filter system can be delivered through one or both of the subclavian artery. In further embodiments, the filter system or portions thereof can be delivered through the femoral artery. Various filter structures are described to perform the desired function of protecting, for example, the carotid arteries during percutaneous heart procedures, such as heart valve replacement. These embolic protection devices can reduce risk associated with heart procedures to more desirable levels so that these procedures can become more clinically acceptable alternatives to open heart procedures. Furthermore, the filters can be also used in conjunction with procedures directly accessing the heart so that emboli which may circulate after restarting the heart are captured by the filters so that they are not circulated to the patient's brain.

The devices described herein are designed to provide protection for the carotid arteries, e.g., left common carotid artery and the right common carotid artery which are spaced apart with respect to their branching relative to the aorta. Thus, a single filter element can span a significant length along the aorta or a plurality of filter elements can be deployed. The right common carotid artery can be protected through the filtering of flow from the aorta into the brachiocephalic artery since this artery leads from the aorta to the right carotid artery as well as to the right subclavian artery at a branch. In some embodiments, a plurality of filters are placed on along a single guide structure such that a distal filter can be deployed to filter flow into the left carotid artery and a proximal filter can filter flow into the brachiocephalic artery. In further embodiments, the filtration system comprises individual filters for filtering flow into the two carotid arteries while the delivery system can be configured to facilitate such delivery. With respect to the placement of individual filters, these can be deployed further downstream the carotid arteries to protect specifically the internal carotid arteries, which supply blood to the brain, and the protection of the external carotid arteries is not as significant since less critical tissues are supplied blood from the external carotid arteries. In additional embodiments, the filter system can be designed to have a single element span between the left common carotid artery and the brachiocephalic artery with controlled flow into the respective arties from the aorta such that the respective flows are filtered. Thus, several filtration system designs are described herein to provide a desired degree of filtration for flow from the aorta to the carotid arteries.

Designs have been proposed for heart valve prostheses that can be delivered and implanted in a percutaneous or endovascular procedure. Furthermore, percutaneous procedures can also be used to perform repairs on heart valves that can reduce or eliminate the use of cardiopulmonary bypass. These procedures and other procedures on the heart generate a risk of emboli being released into the aorta. Emboli in the aorta can flow into the carotid arteries where they can be delivered into a patient's brain, which can result in a stroke and/or other adverse events. In general, the flow of emboli into the descending aorta and/or the subclavian arteries does generate a significant concern. The embodiments of embolic protection devices described herein are designed to filter and/or block flow into the carotid arteries during the valve replacement procedures and other heart procedures. Generally, these procedures are intended to be performed on human patients, although the procedures and devices can also be used on farm animals, pets or other domesticated animals.

In general, it is desirable to maintain flow into the carotid arteries during the procedures so that blood flow to the brain is not disrupted for significant periods of time. However, it is acceptable to block flow into one of the carotid arties for a period of time if flow is maintained into the other carotid artery. Therefore, the devices can be designed to filter flow into both carotid arteries or to block flow into one carotid artery and filter flow into the second carotid artery. Blockage of flow can be performed with a balloon, an extendable occlusive device or the like. Balloon devices are well known in the art. In general, a balloon can be inflated through a lumen of the device with saline or the like. Various filters are known in the art. For example, basket-type filters are commercially available.

Referring to FIG. 1, devices for endovascular procedures on the heart can be brought up to the heart through the descending aorta generally through an incision in the leg. As shown in FIG. 1, aorta is shown with a heart valve delivery catheter 118. Arteries branching from aortic arch 104 are also shown in the diagram. Filtration devices for providing embolic protection can be delivered in some embodiments through an artery in the patient's arm for tracking into right subclavian artery 110 and, optionally into brachiocephalic artery 108. Once the filtration device is delivered into the brachiocephalic artery, one or more filtration elements can be positioned to filter flow into openings of right common carotid artery 112 and left common carotid artery 114.

Alternatively or additionally, a filtration device can also be delivered through the patient's arm for tracking into left subclavian artery 116. Furthermore, filtration devices can be delivered from the descending aorta to filter flow into one or both of the carotid arteries. In general, filtration devices can be delivered on a guide structure that provides for maneuvering the tip of the device to a desired location within the vasculature. Alternatively or additionally, the devices can be delivered on a catheter, which can be delivered over a suitable guide structure.

With the objective of protecting the carotid arteries, such as the common carotid arteries, several filtration system types are described herein. A first class of filtration systems has separate filter elements to protect the individual carotid arteries. These systems may or may not have specific catheter designs to facilitate the delivery of the filter elements. For example, the catheter can be designed to have a side port for the delivery of a filter to the right common carotid artery from the brachiocephalic artery following delivery of the catheter from the right subclavian artery. The filter elements can remain tethered to a guide structure or the like, or the filters can be left un-tethered in position for subsequent retrieval. In some embodiments, a filter element for the left common carotid artery can be delivered through the left subclavian artery to separate the delivery and retrieval of the two separate filters.

In additional embodiments, a plurality of filter elements can be attached to a single guide structure in which one filter element is distal to another filter element. If the guide structure is delivered along the right subclavian artery, the distal filter element can be guided for deployment in the left common carotid artery. The device can then be designed such that the proximal filter element is positioned for deployment in the brachiocephalic artery such that it filters flow to the right common carotid artery.

With respect to the filter elements, various ranges of filter designs are possible. In particular, membrane filter structures have been incorporated into commercial embolic protection filters. Generally, these membrane based structures have large surface areas such that reasonable flow can be maintained through the filter. To provide the desired large surface area, these membrane based filters can have, for example, a windsock shape, a conical shape or the like. Alternative filter designs have been based on three dimensional filtration matrices. These filters can have an advantage with respect to a reduced lateral extent along the blood vessel in the patient while providing excellent filtration with the maintenance of good flow through the filter. Suitable three dimensional filtration matrices can be formed from polymer fibers, and surface capillary fibers have been found to be excellent materials for the formation of filtration matrices, such as with a mat of fibers.

In further embodiments, a filter device can comprise a single filtration element spanning between the opening of the brachiocephalic artery through to the left common carotid artery in which the device is extended to the walls of the vessel to control flow into the arteries from the aorta. The extended portions can form a seal to the walls of the vessel using sealing elements. The structure can be delivered through the right subclavian artery. Filtered flow is then allowed past the sealing elements through the respective interiors of the sealing elements. Suitable sealing elements can be, for example, a balloon, an extending scaffolding with a non-porous cover or the like. In some embodiments, the filtration element can comprise a filtration material connected to the sealing elements such that flow past the sealing elements flows through the filtration material. For example, the filtration material can have a generally cylindrical shape spanning between the sealing elements to provide a large surface area for filtration material. In alternative or additional embodiments, the filtration element can have two filter elements with one filter element associated with each sealing element to filter the flow through that particular sealing element.

In additional or alternative embodiments, the sealing elements can be connected with a tubular member having an opening to accept flow from the aorta. The tubular member can further comprise one or more filter elements within the tubular member between the opening to the aortic flow and the openings past the sealing elements into the respective brachiocephalic artery and the left common carotid artery. The filtration elements can be membrane based, fiber based, a combination thereof or the like. These sealing member based structures can have the advantage that the filter elements do not have to be transitioned between deployed and retrieval configurations in the context of delivery and removal of the filter structure. The sealing members can be designed for convenient deployment and collapse for removal. While the sealing members can reduce the diameter and thus the flow from the aorta, the use of a device in which the filter elements are surrounded within a tubular structure can reduce the risk of release of emboli during the removal of the device without providing any additional steps to the procedure.

In some embodiments, the heart procedures of particular involve an approach to the heart from the descending aorta, around the aortic arch and through the ascending aorta. In particular, endovascular heart valve replacement can be performed as an alternative to heart valve replacement involving open heart surgery. Other heart procedures include, for example, heart valve repair, the repair of defects in the septum separating heart chambers or other heart procedures that result in a stroke risk. However, in additional or alternative embodiments, the heart can be approached through the chest to perform the procedure. Generally, the appropriate filters are deployed at an appropriate stage in the procedure prior to the creation of a significant risk of emboli generation. Some procedures involve cardiopulmonary bypass to maintain circulation during the procedure, and the filters can be deployed to catch emboli that are generated as a result of the bypass procedure itself as well as the procedures on the heart.

As noted above, in some embodiments, a filter device may also be guided through the descending aorta. For example, the filter can be mounted on the exterior of a guide catheter that is positioned with its tip as well as the filter element located within the ascending aorta between the aortic valve and opening into the brachiocephalic artery. The guide catheter along with the mounted filter element can be positioned, for example, before the heart procedure begins or at some other appropriate early time in the procedure. The filter can be delivered to the location in a lower profile configuration, and the filter can be deployed into a deployed configuration that directs the flow in the vessel around the catheter through the filter element so that the down stream flow has emboli removed by the filter.

With the filter in place, the heart procedure can then be performed with the filter providing protection of flow into the body including the common carotid arteries. Tools for performing the heart procedure can be introduced through the guide catheter without any interference by the filter element. Following completion of the heart procedures or at least the steps of the heart procedure creating risk to the patient from emboli generation, the guide catheter along with the filter can be removed. The filter may be transitioned to a configuration to provide for removal, and various auxiliary devices, such as an aspiration catheter or sheath can be used to facilitate the removal of the device, as described in more detail below in the context of specific devices.

In some embodiments, one or more filters are delivered through one or both subclavian arteries. A filter element delivered from the right subclavian artery can be directly positioned for filtering flow into the brachiocephalic artery, or the filter can be steered around a branch point for placement in the right common carotid artery. For placement in the left common carotid artery, a filter element can be delivered through the right subclavian artery, through the brachiocephalic artery, along the aortic arch a relatively short distance prior to entry into the left common carotid artery. A filter can also be delivered into the left common carotid artery from the left subclavian artery following a relatively short transit upstream along the aortic arch. In alternative embodiments, the filters can be placed in an interior carotid artery as an alternative to a common carotid artery.

If a filter is placed within the right carotid artery, this filter would not block access to the left carotid artery from the right subclavian artery by way of the brachiocephalic artery and the aortic arch. However, a filter placed in the brachiocephalic artery can block access to the left carotid artery from the right subclavian artery unless the filter is mounted on a catheter that provides an opening for the second filter to be delivered to the left carotid artery without allowing unfiltered blood to reach the right carotid artery. Thus, some embodiments of the filter system comprise a filter for the brachiocephalic artery mounted on the outside of catheter that is delivered into the patient prior to the delivery through this catheter of the filter for the left carotid artery.

A filter can also be placed within the brachiocephalic artery while providing access to the left carotid artery from the right subclavian artery if the two filters are mounted on a common guide structure. The guide structure then provides for access to the left carotid artery without interfering with the filter for the brachiocephalic artery or causing unfiltered flow that can go to the right carotid artery. Similarly, as noted above, a single filter structure can span between the left carotid artery to the brachiocephalic artery along the aortic arch, which can involve seals at or near the openings to the respective arteries.

For these embodiments with a single structure extending between the left carotid artery and the brachiocephalic artery, the guide structure with a mounted filter or filters, or a separate guide structure generally is delivered into the left carotid artery after originating in the right subclavian artery. The filters and/or sealing elements can be deployed once the tip is appropriately positioned in the left carotid artery. The respective filters and/or sealing elements for the left common carotid artery and the brachiocephalic artery can be simultaneously deployed or sequentially deployed. The order of the deployment may depend on the structure of the device in some embodiments. In particular, the device may be designed to intrinsically simultaneously deploy the elements.

In these embodiments, once the filtration structures are in place to filter the flow into the left carotid artery and the brachiocephalic artery, then the procedures involving the heart can be performed with reduced or eliminated risk of emboli flowing into the carotid arteries. Once the heart procedures are completed, the filter structures can be removed. In some embodiments, the respective filters and/or sealing members can be transitioned to a recovery configuration. In additional or alternative embodiments, an aspiration catheter or sheath can be used to facilitate the retrieval of the filter element(s), and the additional tools may provide some protection against emboli being released from the filter element during retrieval of the filter element.

The filter systems herein provide protection from the release of emboli into the carotid arteries when performing procedures on the heart. In general, the heart procedures can involve access of the heart through the chest and/or through the descending aorta. Through the protection of the carotid arteries, the stroke risks can be significantly reduced. The devices and procedures are designed so that they should not interfere with the devices introduced for performing the heart procedure. With appropriate filtration that does not significantly reduce the flow into the carotid arteries, the filtration protection can be kept in place for heart procedures that take a significant period of time. Thus, the filtration approaches provide a practical approach for the improvement of the outcomes resulting from procedures on the heart.

Filtration Devices

The filtration devices can incorporate various designs to accomplish the objective of filtering flow from the aorta into the right carotid artery and the left carotid artery. In general, the designs can be organized into 4 groups. In a first group, individual filter elements are used for the respective right carotid artery and left carotid artery. In a second group, a plurality of filter elements are mounted onto a common guide structure with a structure that provides for delivery of a distal filter into the left carotid artery while the proximal filter can be positioned for filtration of flow into the brachiocephalic artery. In a third group, a single structure is designed to span from left carotid artery to the brachiocephalic artery such that flow into both arteries is filtered. In a fourth group, a filter element is placed on the exterior of a catheter for delivery into the ascending aorta such that flow around the aortic arch, including flow into the carotid arteries, is filtered. Devices for performing the heart procedure can be delivered through the catheter with the filter element.

1. Individual Filter Elements for Common Carotid Artery Filtering

The filtration systems within this group have separate elements to protect the respective left carotid artery and the right carotid artery. The filters can be placed in the common carotid arteries, or alternatively one or both filters can be placed past the common carotid artery and in the respective internal carotid artery. In general, the filters or embolic protection devices can be tethered while the filters are deployed to filter flow, or alternatively or additionally one or both of the filters can be left in the vessel un-tethered at a position to provide desired filtration of flow. An un-tethered filter can be recovered some time following the completion of a heart procedure. Suitable tethers include, for example, guide structures. Guide structures, such as guidewires or integrated guiding devices, generally provide flexibility and maneuverability that provides for placement of the filters at desired positions. In some embodiments, a filter device comprises a single guide structure and a single filter element that are tracked into the brachiocephalic or a common carotid artery. If the filter is deployed in an un-tethered configuration, a guide structure or the like can be designed as a deployment tool, such as a sheath, for releasing the filter at the selected location. An appropriate retrieval tool can be used to recover an un-tethered filter following completion of the procedures that motivated the placement of the filters.

Appropriate filter elements may be formed from a variety of materials and can be designed such that sufficient blood flow is maintained even under moderate embolic loading. In some embodiments, filter elements may comprise a three dimensional filtration matrix that provides for the capture of emboli on the surface of the filter and/or within the filtration matrix. The filtration matrix can provide for a large number of alternative flow pathways through the matrix such that good flow can be maintained through the filter even with a significant emboli loading. Additionally or alternatively, filter elements may comprise a basket type filter element that comprises a filter membrane having distinct pores and generally a frame supporting the membrane. The basket opening can be place across the vessel so that flow is directed into the basket where emboli are filtered. In further embodiments, filter elements can combine three dimensional filtration matrices along with membrane based filter elements.

Figure 2A:
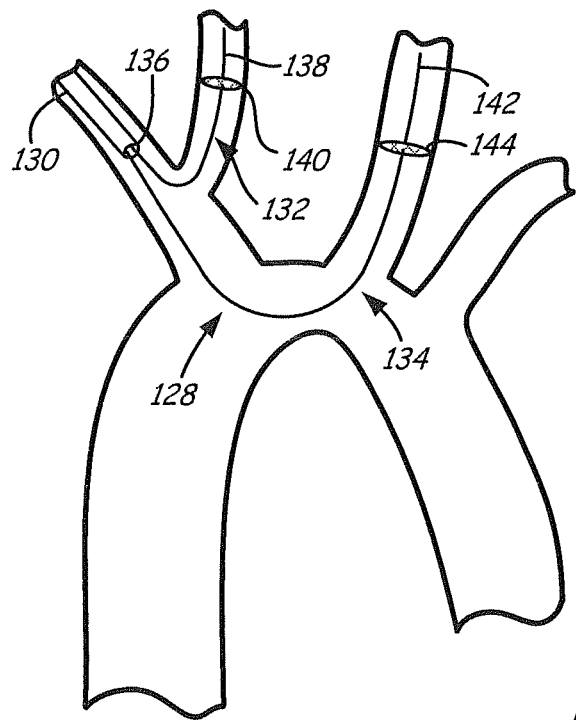
FIG. 2A is a sectional view of the aortic arch depicting two independent filter elements placed respectively in the right carotid artery and left carotid artery through the right subclavian artery.

Referring to FIG. 2A, an embodiment is shown in which the protection device comprises two separate filter elements that are delivered from a guide catheter. One of the filter elements is deployed in the left common carotid artery, and the other filter element is deployed in the right common carotid artery. On or more retrieval catheters can be used to facilitate the recovery of the filter devices. For example, fiber-based filter devices can be recovered effectively using an aspiration catheter as described in U.S. patent application 2007/0060944A, now issued Pat. No. 8,021,351 to Boldenow et al., entitled "Tracking Aspiration Catheter," incorporated herein by reference. In alternative embodiments, the filter in one of the two carotid arteries can be replaced with an occlusive device, such as a balloon.

Figure 2B:
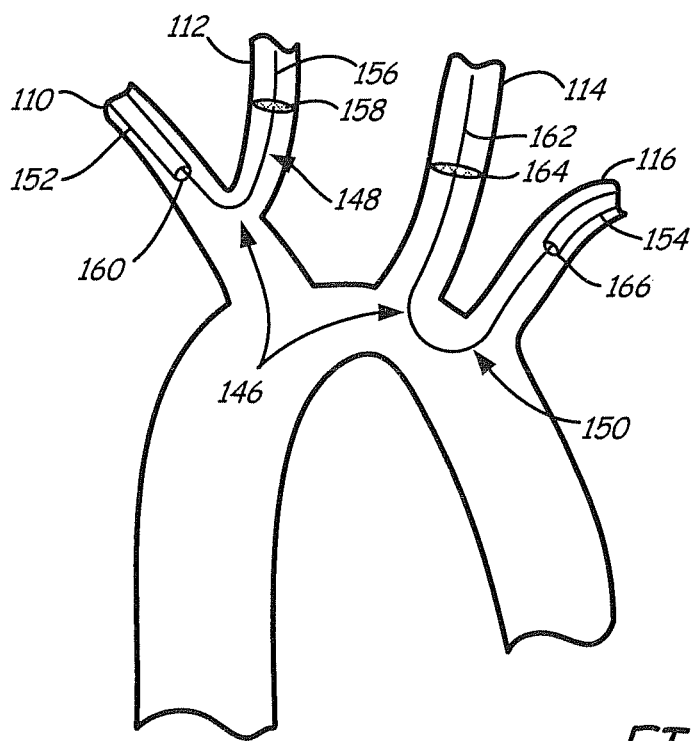
FIG. 2B is a sectional view of the aortic arch depicting two independent filter elements placed into the right carotid artery through the right subclavian artery and into the left carotid artery through the left subclavian artery.

FIGS. 2A and 2B illustrate filtration systems wherein independent filter elements are deployed, respectively, into the left common carotid artery and right common carotid artery. Referring to FIG. 2A, filter system 128 comprises a catheter 130, a first filter device 132 and a second filter device 134. Catheter 130 comprises a central lumen 136, through which first filter device 132 and second filter device 134 can be delivered. In some embodiments, catheter 130 may comprise two lumens so that filter devices 132, 134 can be separately tracked through catheter 130. Filter device 132 can comprise tether or guide structure 138 and filter element 140. Similarly, filter device 134 can comprise tether or guide structure 142 and filter element 144.

Filter elements 140, 144 can be attached to guide structures 138, 142, respectively, so that they may be independently or sequentially actuated between their delivery and deployed configurations. In some embodiments, a filter element may comprise a self-expanding filter formed form shape memory polymers or metal alloys or other suitable material as described below. In such embodiments, the guide structure may comprise a guidewire and the filter element may be welded, glued, or otherwise suitably attached to the guidewire. In other embodiments, a guide structure may be an integrated guiding device comprising a corewire and an overtube in which relative movement of the corewire and overtube can transition the attached filter element between its delivery configuration and deployed configuration. Suitable filter elements are described further below.

Referring to FIG. 2B, a filtration system 146 comprises two independent filtration devices 148, 150 deployed through two separate catheters 152, 154. Filtration device 148 comprises a tether or guide structure 156 and a filter element 158 attached to the tether 156 at or near its distal end. The distal end of tether 156 and filter element 158 may be tracked through a lumen 160 within catheter 152. Similarly, filter device 150 comprises a tether or guide structure 162 and a filter element 164 attach at or near the distal end of tether 162. The distal end of tether 162 and filter element 164 may be tracked through a lumen 166 within catheter 154. As depicted in FIG. 2B, catheter 152 is positioned within right subclavian artery 110, and filter element 158 is positioned within right common carotid artery 112 on tether 156. Furthermore, catheter 154 is positioned within left subclavian artery 116, and filter element 164 is positioned within left common carotid artery 114 on tether 162. Alternatively, filter 158 and/or filter 164 can be placed in the corresponding internal carotid artery.

Referring to FIG. 3, in this embodiment a filter element is deployed in the left common carotid artery. The guide catheter has an element mounted along its exterior surface. This element can be a filter or an occlusive element, such as a balloon. FIG. 4 is an embodiment similar to FIG. 2, in which the guide catheter has a side port that provides for the delivery of a device into the right common carotid artery through the side port. The device deployed into the right common carotid artery can be an occlusive device such as a balloon.

Figure 3A:
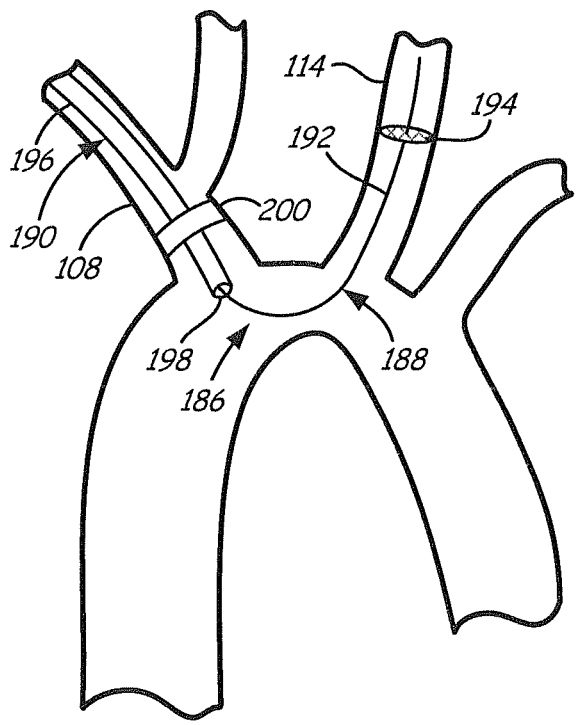
FIG. 3A is a sectional view of the aortic arch depicting a catheter with an external filter deployed to filter flow into the brachiocephalic artery and a filter device deployed through the catheter with a filter element deployed in the left carotid artery.
Figure 3D:
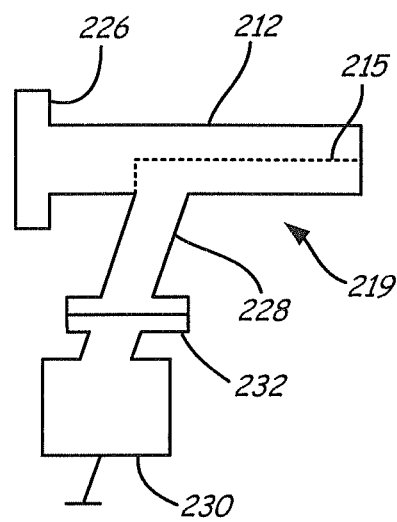
FIG. 3D is a fragmentary side view of the proximal end of the catheter of FIG. 3B with hidden structure shown in phantom lines.
Figure 3B:
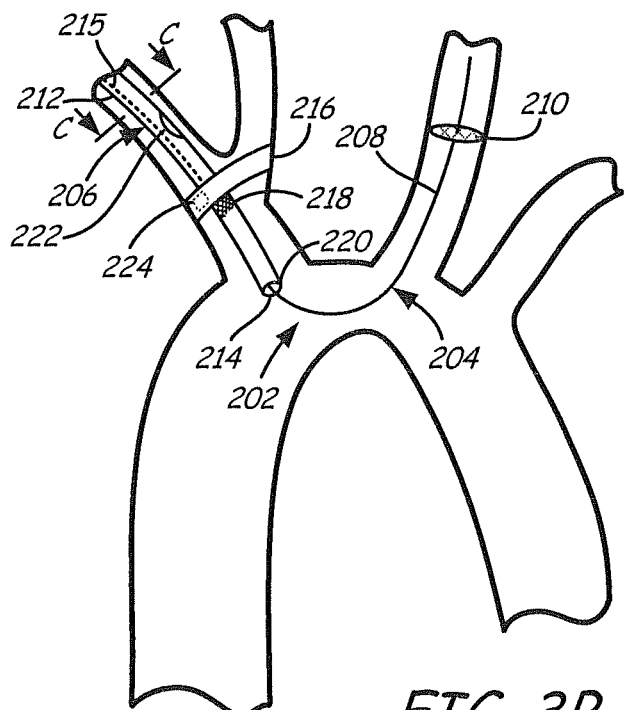
FIG. 3B is a sectional view of the aortic arch depicting a catheter with an external occlusive element and an internal filter leading to a flow port proximal to the occlusive element, and filter device deployed through the catheter with a filter element deployed in the left carotid artery.
Figure 4:
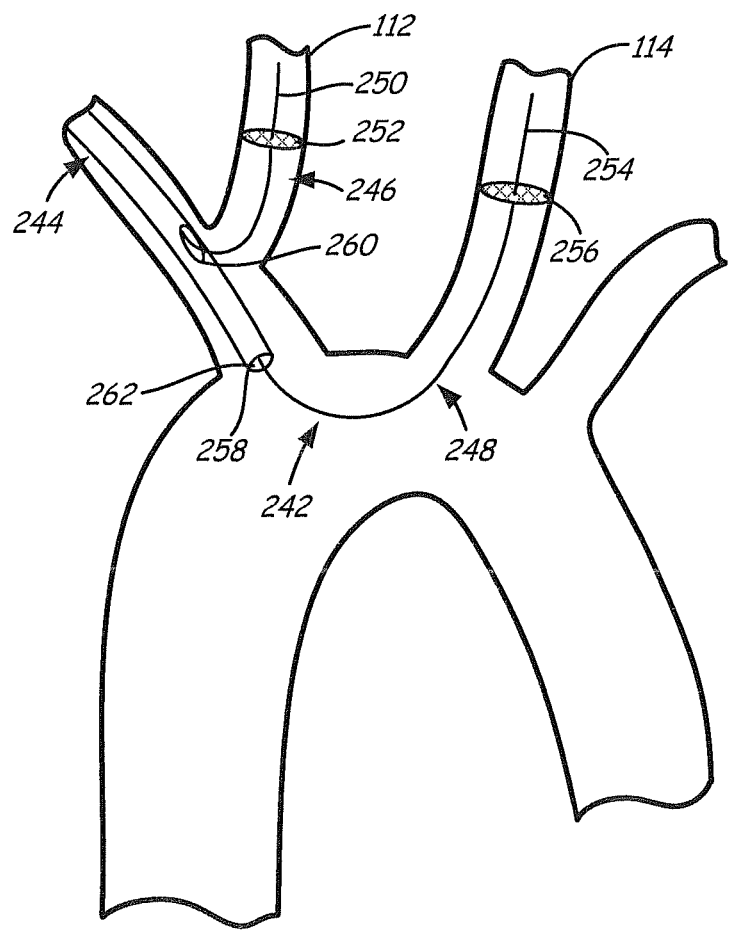
FIG. 4 is a sectional view of the aortic arch depicting a catheter with a distal opening and a side opening along with a first filter device deployed through the distal opening of the catheter and a second filter device deployed through the side opening of the catheter.

Referring to FIGS. 3A and 3B, filter systems are shown in which a delivery catheter comprises a filter and/or an occlusive element which can replace one of the filter devices with respect to filter system 130 of FIG. 2A. Referring to FIG. 3A, filter system 186 comprises a filter device 188 and catheter 190. Filter device 188 comprises a tether or guide structure 192 and filter element 194. Catheter 190 comprises tubular element 196 with a central lumen 198, and filter element 200 that is attached at or near the distal end of tubular element 196. Filter element 200 can be designed with respect to configuration and size for deployment in brachiocephalic artery 108. Filter device 188 can be designed to extend from central lumen 198 for placement of filter element 194 in left carotid artery 114.

Figure 3C:
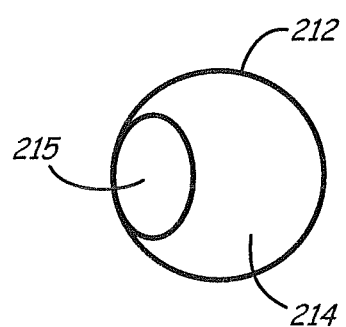
FIG. 3C is a sectional view of the catheter of FIG. 3B taken along line C-C.

Referring to FIG. 3B, filter system 202 comprises filter device 204 and catheter 206. Filter device 204 comprises a tether or guide structure 208 and a filter element 210. Catheter 206 comprises tubular element 212 with a lumen 214 and an inflation lumen 215, occlusive element 216 and filter element 218. Tubular element 212 has a distal port 220 and a filtered flow port 222. A cross section of tubular element 212 is shown in FIG. 3C. Occlusive element 216 can be, for example, a balloon or other extendable, non-porous structure. Inflation lumen 215 can interface with occlusive element 216 at inflation port 224. Filter element 218 is located within lumen 214 such that flow between distal port 220 and filter flow port 222 is filtered by filter element 218. The proximal end of catheter 190 is shown in FIG. 3D. In this embodiment, the proximal end of tubular element 212 has a fitting 226, such as a Leur fitting. A side arm 228 connects an inflation source 230, such as a syringe, with inflation lumen 215, and inflation source 230 is connected to arm 228 at fitting 232.

Filter element 218 may be formed from any suitable filter material or combination thereof. Due to the location of filter element 218 within tubular element 212, filter element 218 can be fixedly attached in a desired configuration. For example, filter element can comprises a fiber filtration matrix, such as surface capillary fibers, in a woven or unwoven mat, a porous filter membrane, or a combination thereof. Suitable porous membranes can be formed from comprising a sheet comprising polymer and/or metal. Guide structure 208 can slide through filter element 218, for example, with a gasket or washer attached within filter element 218. A gasket or washer can be formed from polytetrafluoroethylene or the like to produce a low friction interface with guide structure 208. Filter element 218 can be positioned within tubular element 212 while leaving a distal section into which filter element 210 can be positioned during delivery into the vessel and withdrawal from the vessel. Filter device 204 can be pre-loaded with respect to catheter 206 prior to placement within the patient. With filter system 186, aortic blood flow into brachiocephalic artery 108 through port 222 is filtered by filter element 218 and enters the right subclavian artery 173 and right common carotid artery 112.

FIG. 4 illustrates an alternative embodiment of a filtration system similar to the system shown in FIG. 2A. Referring to FIG. 4, filtration system 242 comprises catheter 244, first filter device 246 and second filter device 248. First filter device 246 and second filter device 248 are analogous to first filter device 132 and second filter device 134 of FIG. 2A. First filter device 246 comprises tether or guide structure 250 and filter element 252 and is designed to extend from catheter 244 into the right carotid artery 112. Filter device 248 comprises tether or guide structure 254 and filter element 256 and is designed to extend from catheter 244 into the left carotid artery 114.

Catheter 244 comprises a distal port 258 and a side port 260. Distal port 258 and side port 160 are designed for the delivery of a filter element from lumen 262 within catheter 244 such that the filter element and a tether extend out form the respective port to a deployment position. A deflection control catheter, such as catheter 244 can provide support for a guide structure making a sharp turn since the side port can help direct the tip of the guide structure in a desired direction. Catheter 244 can be formed with an appropriate diameter to provide for the delivery of two guide structures without interference between the guide structures. Deflection catheters are described further in published U.S. patent application 2007/0208302 to Webster et al., entitled "Deflection Control Catheters, Support Catheters, and Methods of Use," incorporated herein by reference.

Figure 5:
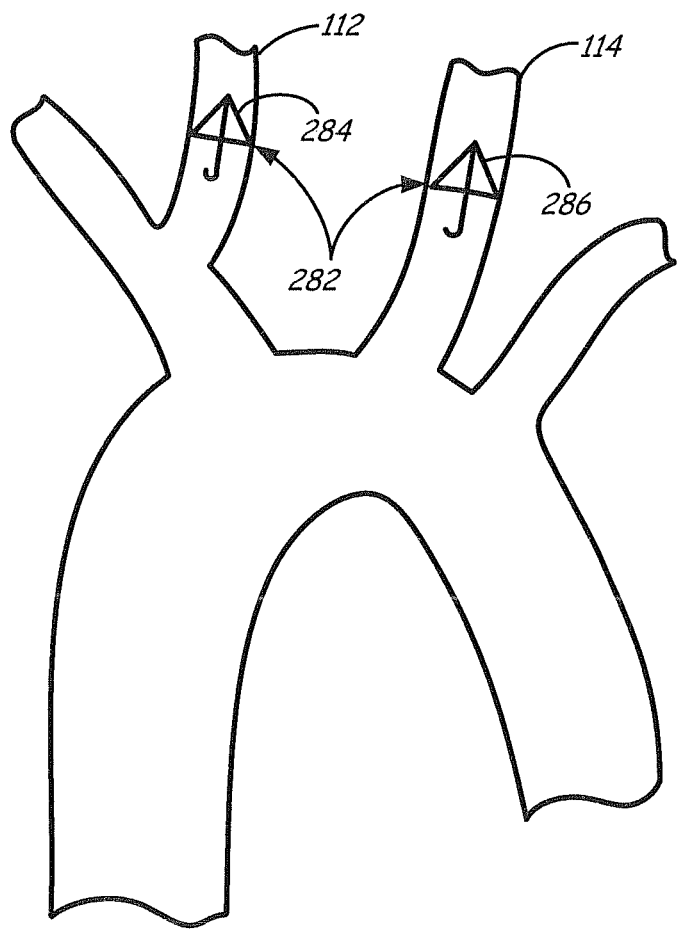
FIG. 5 is a sectional view of the aortic arch depicting an un-tethered filter deployed in the right carotid artery and an un-tethered filter deployed in the left carotid artery.

Referring to FIG. 5, a filtration system 282 comprises detachable filters 284, 286 that can be deployed in an un-tethered format within the arteries to provide desired filtration. As shown in FIG. 5, filter elements 284, 286 are deployed into the right carotid artery and left carotid artery, respectively. As described further below, filters 284, 286 may be deployed using an appropriate delivery tool, and following completion of a heart procedure that generates the risk of emboli production, a removal tool can be used to withdraw the filters so that they do not remain within the arteries.

While FIG. 5 shows un-tethered filters with one filter in the right common carotid artery and one filter in the left common carotid artery. In alternative embodiments, an un-tethered filter can be placed in the brachiocephalic artery, and/or one or both filters can be placed in a corresponding interior carotid artery. Furthermore, in some filter systems, on filter can be tethered while a second filter is un-tethered. For example, an un-tethered filter can be placed in the left common carotid artery, and a tethered filter can be placed in the right common carotid artery. For embodiments with an un-tethered filter in the left common carotid artery, the aorta can be free of structures relating to the carotid filtering during portions of the procedure on the heart.

In the embodiments above in FIGS. 2-5, the filtration systems can comprise various filter elements for appropriate deployment in association with a guide structure or for un-tethered deployment. Filter elements generally are designed to filter aortic blood flow into the left carotid artery or right carotid artery such that sufficient flow is maintained even under moderate embolic loading. In some embodiments, to perform the desired filtration, the filters can be designed to be deployed into the brachiocephalic artery, right carotid artery, and/or left carotid artery. For embodiments in which filter elements are deployed in association with a guide structure or in an un-tethered format, the filter elements generally can be adapted from designs for other applications. In general, filter elements may comprise a three dimensional filtration matrix, a filter membrane, combinations thereof or the like.

A basket-type filter generally has a filtration membrane having pores drilled, woven, molded or otherwise formed through the two-dimensional membrane. The size of the pores can be selected to allow passing beneficial blood components while blocking emboli with sizes exceeding the pore sizes. The shape of the basket can have the shape of a cone, a wind sock or similar shape. Generally, the filtration membrane can be supported by a frame, struts or the like to provide a desired shape to the filter structure. The expanded surface area of the basket can reduce clogging of the membrane for a particular loading of emboli. Suitable sizes of the pores can be determined for a particular application. For general applications in blood vessels, pores with a diameter from 50 microns to 250 micron can be suitable. The porous membrane may comprise, for example, a polymer, such as polyurethane or polyester, metal or other suitable material that is attached to the frame member.

Generally, a frame member and/or struts of a basket filter can be made, for example, from a biocompatible metal, a suitable polymer or a combination thereof. Suitable biocompatible metals include, for example, titanium, cobalt, stainless steel, nickel, iron alloys, cobalt alloys, such as Elgiloy®, a cobalt-chromium-nickel alloy, MP35N®, a nickel-cobalt-chromium-molybdenum alloy, and Nitinol, a nickel-titanium alloy. In some embodiments, the frames can be designed to spontaneously assume an extended configuration when released in the vessel, while in other embodiments the frames can be actuated to assume a deployed configuration. Commercially available basket filters come in a variety of frame sizes corresponding to the basket diameter. The frame size can be chosen such that the edge of the basket contacts the vessel wall without damaging the vascular wall. Commercial basket filters include, for example RX Accunet®, an embolic protection device from Abbott Laboratories, IL, USA, Filter-Wire™ from Boston Scientific Inc, MA, USA, and Spi-derFX™ embolic protection device, from ev3, Inc., MN, USA, which comprises a basket filter with a windsock shaped Nitinol mesh basket that serves as the filter member. Self expanding basket filters are described further, for example, in U.S. Pat. No. 6,740,061 to Oslund et al., entitled "Distal Protection Device," incorporated herein by reference. Actuatable filter elements with a filtration membrane are described further in U.S. Pat. No. 6,146,396 to Kónya et al., entitled "Declotting Method and Apparatus," and U.S. Pat. No. 6,663,652 to Daniel et al., entitled "Distal Protection Device and Method," both of which are incorporated herein by reference. To aid with the selection of a filter size, reference vessel diameters may be obtained via angiography, quantitative angiography, ultrasound, or other suitable technique.

Matrix based filters generally can comprise a network of interconnected and circuitous flow pathways through a three-dimensional mass of material. The availability of alternate flow pathways allow such matrix based filters to maintain good flow even with moderate embolic loading. Generally a low pressure drop can be maintained across the filtration device with a three dimensional filtration matrix after it is deployed. In some embodiments, a filter with a three dimensional filtration matrix can have a significantly smaller lateral extent along a blood vessel relative to basket type filter designs since the flow pathways through the filter matrix reduces the need for a large surface area to maintain flow under a moderate embolic loading.

In some embodiments, matrix material may comprise a swelling polymer such as a hydrogel or shape memory fibers. Hydrogels are hydrophilic materials comprising polymers that are cross-linked to prevent them from being water soluble. When such materials contact aqueous solutions such as blood or other bodily fluids, the material expands due to absorption of fluid/liquid into the structure of the material. These types of filtration materials are described further in U.S. Pat. No. 7,303,575 to Ogle, entitled "Embolism Protection Devices," incorporated herein by reference.

In further embodiments, filters with three dimensional filtration matrices may comprise a bundle of fibers that are deployed into the filtration matrix. Suitable fibers include, for example, surface capillary fiber (SCF) fibers. SCF fibers comprise fibers with channels/grooves (surface capillaries) that run along the length of the fiber or a portion thereof. The presence of the channels increases the surface area of the fiber relative to a non-channeled fiber with the same radius ("round fiber"). For example, 4DG™ Fiber, an SCF fiber commercially available from Fiber Innovation Technology, Inc., Johnson City, Tenn., typically has 3 times the specific surface area of a comparable round fiber.

Referring to FIGS. 2-4, guide structures associated with tethered filters can comprise a guidewire, an integrated guiding device or the like. As described herein, a guidewire has a long thin shape, which can have a circular or non circular cross section. In some embodiments, the guidewire can be, for example, a solid wire or a coil with a hollow interior, optionally with a cover over the surface. Generally a guidewire is flexible for maneuvering within a patient's vasculature or other vessels within the patient, and the tip may be bendable to facilitate steering of the guidewire.

As used herein, an integrated guide structure may be similar to a guidewire, but the integrated guide structure may comprise a structure with components that move relative to each other. For example, an integrated guide structure can have a corewire and an overtube such that the core wire and overtube can move longitudinally relative to each other. In some embodiments, a torque coupler can couple the rotational motions of the corewire and overtube, which may also limit the range of relative longitudinal movement. Coils can also be added to the structure to increase the flexibility of the structure near the distal tip.

Figure 6A:
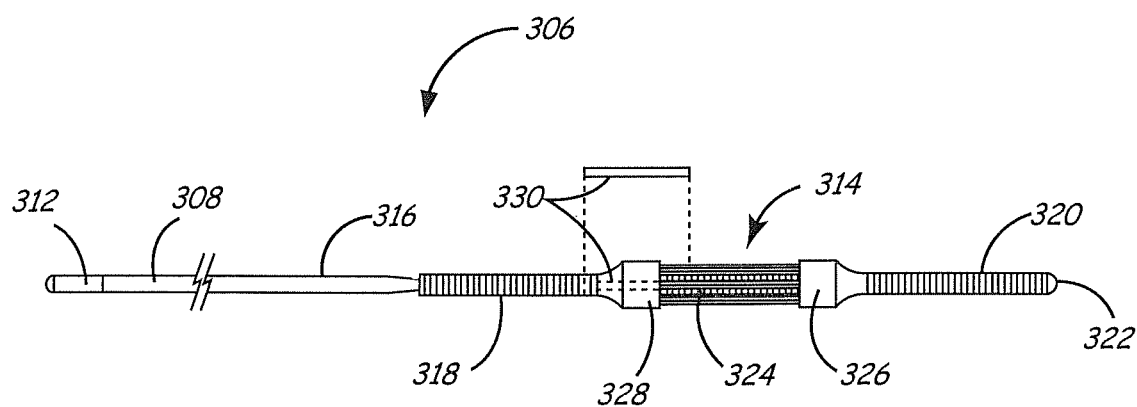
FIG. 6A is a side view of a filter device having a bundle of fibers forming a filter element on an integrated guide structure, in which the filter element is shown in a low profile delivery configuration.
Figure 6B:
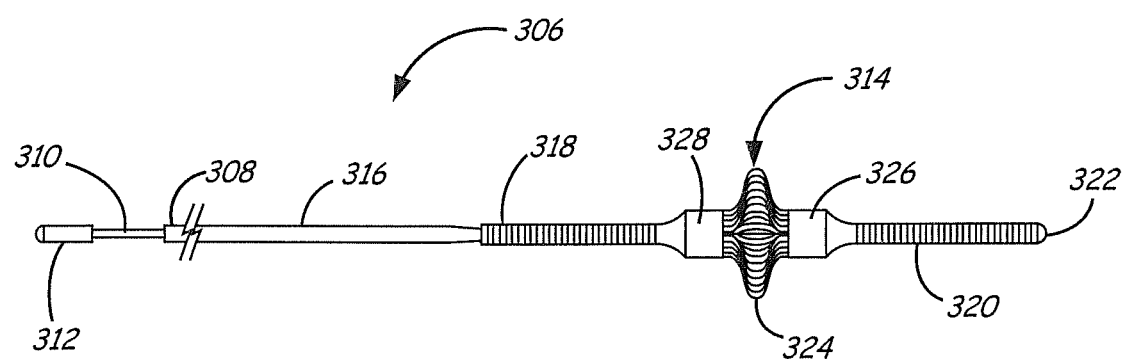
FIG. 6B is a side view of the filter device of FIG. 6A in which the filter element is in a deployed extended configuration.

Referring to FIGS. 6A and 6B, a filter device 306 comprising an overtube 308, a corewire 310 that extends within overtube 308, a handle 312 and a filter element 314. Referring to the side view in FIG. 6A, overtube 308 has a tapered section 316 at its distal end. In this embodiment, a proximal coil 318 is abutted against and secured to tapered section 316. Corewire 310 is covered with a distal coil 320 at its distal end. Distal coil 320 is connected with solder and a weld 322, although other attachment approaches can be used. Overtube 308, corewire 310, proximal coil 318, distal coil 320 and grip 312 can all be formed from stainless steel, although other suitable materials can be used as desired. Suitable actuation tools to provide for control of the relative movement of the corewire and overtube are described further in copending U.S. patent application Ser. No. 12/218,306 filed Jul. 14, 2008 to Galdonik et al., entitled "Fiber Based Medical Devices and Aspiration Catheters," incorporated herein by reference.

In this embodiment, filter device 314 comprises a bundle of SCF fibers 324 attached at first attachment 326 and second attachment 328. A 0.1 inch long tube 330, which can be formed from polyimide polymer, is located within the second attachment 328 with corewire 310 extending through the tube. The fibers are swaged/crimped/bonded at the two attachments 326, 328, such as with radio-opaque bands. First attachment 326 is attached to move with corewire 310, and second attachment 328 is attached to move with overtube 308 along with proximal coil 318. After crimping, the fiber bundles can be bonded at each end with an adhesive, such as cyanoacrylate, and/or fused together with heat bonding.

The length of the fiber generally is chosen so that it is at least twice as long as the radius of the vessel at the deployment site. The length can be chosen so that in the deployed configuration, filter element 227 effectively provides embolic protection while maintaining flow and without damage to the vascular wall. As mentioned above, reference vessel diameters may be estimated with angiography or other suitable method. Additionally, the fibers are generally aligned in a low profile configuration for delivery, and the fibers flare outward from the corewire in a deployed configuration. The SCF fiber properties can be chosen so that when filter element 324 is in its deployed configuration, flow is adequately maintained in the vessel even with significant embolic loading. Further discussion on the selection of appropriate fiber characteristics as well as suitable materials for such an embodiment can be found in published U.S. Patent application number 2006/0200047A, now issued Pat. No. 8,092,483 to Galdonik et al., entitled "Steerable Device Having a Corewire Within a Tube and Combination with a Functional Medical Component," incorporated herein by reference. Commercial filters with a structure similar to the device in FIGS. 6A and 6B with SCF fibers are available from Lumen Biomedical, Inc. under the name FiberNet®.

In some embodiments, a filter element can comprise a combination of a three dimensional filtration matrix with a basket type filter. For example, a fiber-based filter can be located within a basket such that flow passes first through the filtration matrix and then through the filtration membrane. The basket can form a stable frame to support the fiber-based filtration membrane, which can be desirable for high flow vessel. The basket can facilitate removal of the filtration matrix for certain deployed placements.

Figure 7:
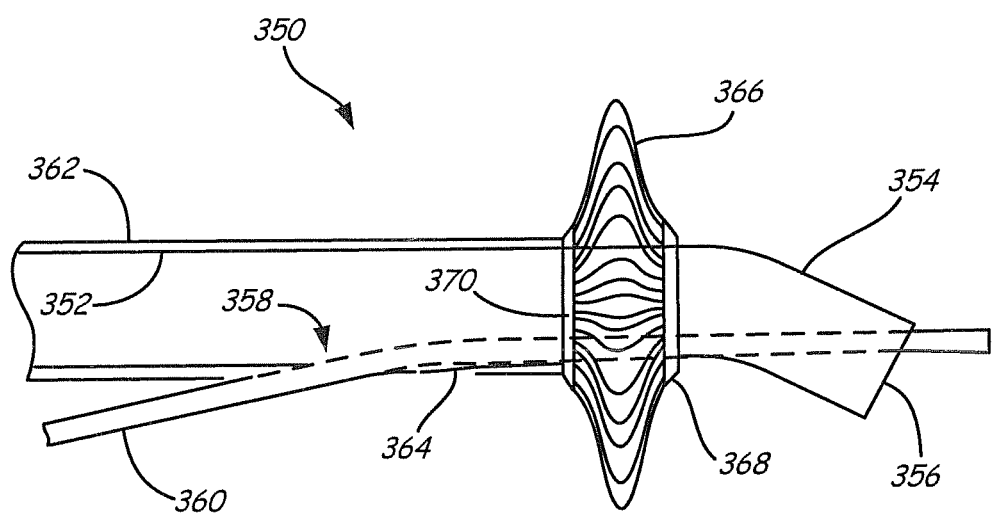
FIG. 7 is a fragmentary side view of the distal end of a rapid exchange catheter having a filter that extends outward from the surface of the catheter and with a bent tip that provides for improved tracking.

The filter system described in FIG. 3A has a catheter with a filter mounted on the exterior of the catheter. Catheters, which can be adapted for current filtration applications, are described, for example, in more detail in published U.S. patent application 2008/0172066 to Galdonik et al., entitled "Embolectomy Procedures With a Device Comprising a Polymer And Devices With Polymer Matrices and Supports," incorporated herein by reference. A suitable embodiment of a catheter with an external filter is shown in FIG. 7, which also has a rapid exchange structure. Referring to FIG. 7, catheter 350 comprises a tubular element 352 with a bent tip 354 and a distal opening 356. A rapid exchange port 358 provides for insertion of guide structure 360 into tubular element 352, and guide structure 360 can exit tubular element 352 at distal opening 356.

Overtube 362 rides over tubular element 352. Overtube 362 can have a slit or similar structure 364 to provide for the relative movement of overtube 362 and tubular element 352 without interference from guide structure 360. Since overtube 362 generally does not need to hold liquid since tubular element 352 can define a central lumen, overtube 362 can have a structure that is only tubular in the sense of being able to ride over tubular element 352 and transmit longitudinal movement from the proximal end of the device to the distal end of overtube 362. Fibers 366 attach at a first end to tubular element 352 at first band 368, and fibers 366 attach at a second end to overtube 362 at second band 370. Relative movement of overtube 362 and tubular element 352 can be used to transition fibers 366 between a deployed, flared out configuration and a straighter configuration for delivery into and removal from a vessel. As shown in FIG. 7, fibers 366 are in a flared out, deployed configuration, but a distal shift of tubular element 352 relative to overtube 362 places the fibers in a straighter lower profile configuration. Fibers 366 are generally arranged in a bundle, and fibers 366 can comprise SCF fibers to provide desirable filtration.

In some embodiments, un-tethered filter elements are placed in the vessels to provide desired filtration. These filtration systems are discussed above in the context of FIG. 5. Commercial un-tethered filters are available for deployment in veins, in particular the vena cava. These vena cava filters can be adapted for temporary placement for filtering flow into the carotid arteries. Filtration membranes and/or filtration matrices can be added to the vena cava filter designs to provide greater control over emboli migration. Vena cava filters are described further, for example, in U.S. Pat. No. 6,126,673 to Kim et al., entitled "Vena Cava Filter," incorporated herein by reference. Un-tethered filters with three dimensional filtration matrices are described further in U.S. Pat. No. 7,303,575 to Ogle, entitled "Embolic Protection Devices," incorporated herein by reference. In some embodiments, self expanding un-tethered filters can be delivered from a catheter, in which the filters are pushed out from the catheter, that constrains the filter in a delivery configuration. Upon release of a self-expanding filter, the filters deploy in the vessel. In alternative embodiments, a specific deliver device can be used to deliver the un-tethered filter. Similarly, a retrieval device can be used to recover an un-tethered filter. A retrieval device can grip or otherwise engage the filter. Suitable retrieval devices for some un-tethered filter designs are described further in U.S. Pat. No. 6,726,621 to Suon et al., entitled "Retrieval Devices for Vena Cava Filter," incorporated herein by reference. Similarly, grippers or micro-forceps that can be delivered into the vasculature through catheters can similarly be used to grip and remove un-tethered filter, which in some embodiments can be pulled into a sheath or distal end of an aspiration catheter.

In general, any of the catheters described herein above or below can comprise an over-the-wire design or a rapid exchange design. In a rapid exchange format, a guide structure exits a lumen through the side of the catheter generally toward the distal end of the catheter such that the guide structure only engages the catheter over a portion of the length of the catheter. The catheters can be made from one or more biocompatible materials, including, for example, metals, such as stainless steel or alloys, e.g., Nitinol, or polymers such as polyether-amide block co-polymer (PEBAX®), nylon (polyamides), polyolefins, polytetrafluoroethylene, polyesters, polyurethanes, polycarbonates or other suitable biocompatible polymers. In some embodiments, the catheter can comprise a polymeric tubular structure reinforced with braided metal embedded in the polymer. Also, the catheter tip may be curved or bent to improve tracking of the catheter on a guide structure. Rapid exchange catheters are described further in published U.S. patent application 2007/0060944A, now issued Pat. No. 8,021,351 to Boldenow et al., entitled "Tracking Aspiration Catheter," incorporated herein by reference.

2. A plurality of Filter Elements on a Common Guide Structure

In some embodiments, a single guide structure can be constructed using a plurality of filter elements that are suitable to provide simultaneous filtration of aortic blood flow into the left and right carotid arteries. Such filter devices can comprise a single guide structure with an attached proximal filter element and distal filter element. The proximal filter element generally can be tracked into the brachiocephalic artery and deployed, and the distal filter element can be tracked through the brachiocephalic artery and into the left carotid artery for deployment. In this configuration, the flow through the distal filter is in a proximal to distal direction relative to the orientation of the guide structure, and the flow through the proximal filter is in a distal to proximal direction relative to the orientation of the guide structure. In some embodiments, the filters can be designed with appropriate orientations based on the expected flow directions.

The filters generally have a low profile delivery configuration and an extended deployed configuration. In some embodiments, the guide structure can comprise one or more corewires associated with an overtube, such that relative movement of the corewire(s) and the overtube can be used to transition the filters between their low profile configuration and the extended configuration. The filter device can be constructed so that the proximal filter element and distal filter element are either independently actuated or simultaneously actuated between their low profile delivery configuration and deployed configuration. If the two filter elements can be independently transitioned between configurations, the proximal filter element and the distal filter element can be sequentially transitioned between configurations to facilitate removal of the devices, as described further below. In some embodiments, one or both filter elements can be self extending following release from a sheath or the like.

Figure 8A:
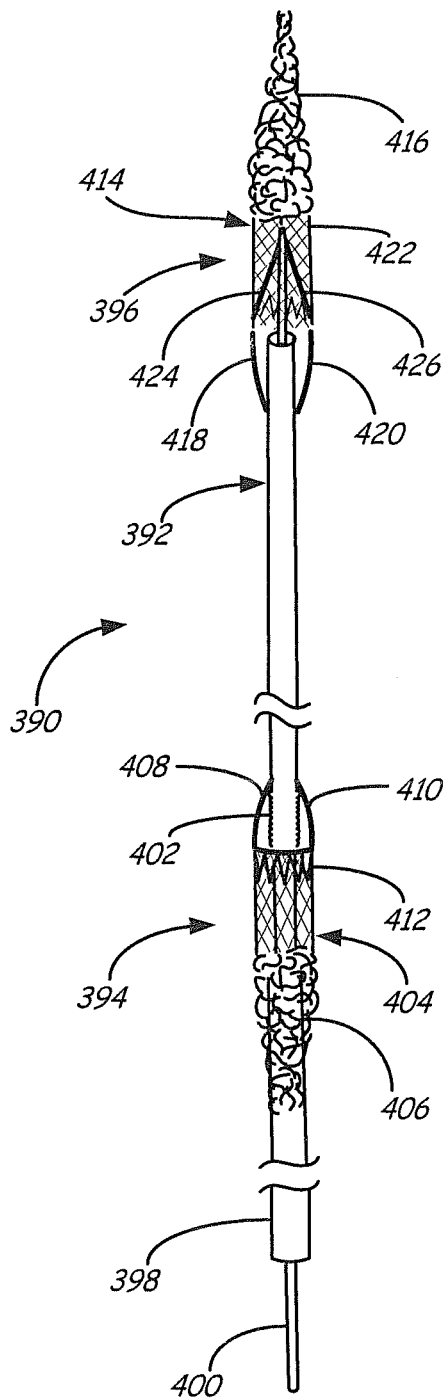
FIG. 8A is a side view of a filter device having a proximal filter element and a distal filter element along a single integrated guiding device with a corewire that provides for the deployment and collapse of the filter elements, in which the filter elements are displayed in a low profile delivery configuration.
Figure 8B:
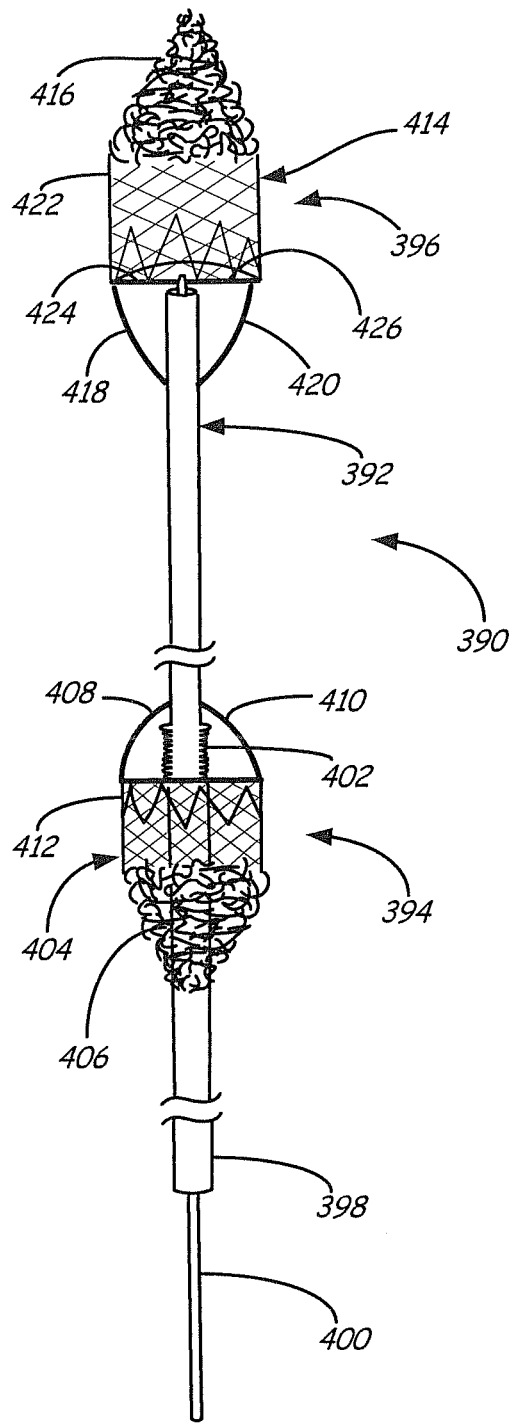
FIG. 8B is side view of the filter device of FIG. 8A in which the filter elements are shown in their extended deployed configuration.

FIGS. 8A and 8B show an embodiment with two filter elements that are attached to a common guide structure. In this embodiment, the two filters generally are simultaneously deployed and subsequently collapsed. Filter device 390 comprises guide structure 392, proximal filter element 394 and distal filter element 396. Guide structure 392 comprises an overtube 398 and corewire 400. Overtube 398 and corewire 400 can comprise elements of one or more torque couplers that provide torque coupling between overtube 398 and corewire 400. Generally, overtube 398 can move longitudinally relative to corewire 400, although a torque coupler or other structure may limit the extent of the relative motion. Suitable torque couplers can have a lock and key type of interface between structures along the surface of corewire 400 and the inner surface of overtube 398. Overtube 398 can comprise a contracting section 402 near proximal filter 394 which allows for slight contraction of overtube 398 at that location decreasing the overall length of overtube 398 to change the configuration of proximal filter 394. Contracting section 402 can be formed from weakened segments that are designed to fold upon the application of a moderate force, such as with an accordion type structure. Overtube 398 and corewire 400 may be formed from suitable materials for guide structures as described above.

In general, proximal filter 394 and distal filter 396 can have any reasonable construction consistent with the attachment to the integrated guide structure. In particular filter element designs described above for individual placement of filter elements can be adapted for a tandem placement of dual filters on a single guide structure. The placement of two filters based on three dimensional filtration matrices on a single integrated guide structure is described further in published U.S. patent application 2008/0172066A to Galdonik et al., entitled "Embolectomy Procedures With a Device Comprising a Polymer and Devices with Polymer Matrices and Supports," incorporated herein by reference. Filters with baskets should be oriented so that the opening of the basket is oriented toward the direction of the incoming flow. Thus, distal filter 396 can have an opening facing the proximal direction relative to the guide structure, and proximal filter 394 can have an opening facing the distal direction relative to the guide structure. In some embodiments, one or more of the filters can have both a basket shaped frame and a three dimensional filtration matrix.

As shown in FIGS. 8A and 8B, filter elements 394 and 396 comprise a frame with an associated filter matrix. Proximal filter element 394 comprises frame 404 and fiber-based filtration matrix 406. Frame 404 comprises struts 408, 410 and extendable cylindrical section 412. Struts 408, 410 are configured to bend when contracting section 402 is contracted, and the bent struts extend cylindrical section 412 into an extended configuration. Cylindrical section can comprise a pleated structure that unfolds to the extended structure upon deployment. Filtration matrix 406 can comprise a mat of fibers, such as SCF fibers. In some embodiments, one end of the fibers is attached to overtube 400 and another end is attached to extendable cylindrical section 412 such that the filtration matrix 406 extends across the vessel when cylindrical section 412 is extended with an opening of the cylindrical section oriented toward the distal end of filter device 394. Fibers can be attached, for example, with adhesive, heat bonding, mechanical clamping or combinations thereof.

Similarly, distal filter 396 comprises frame 414 and fiber based filtration matrix 416. Frame 414 comprises struts 418, 420 and extendable cylindrical section 422. Struts 418, 420 attach at one end to overtube 398 and at another end to cylindrical section 422. Cylindrical section struts 424, 426 connect the lower edge of cylindrical section 422 with corewire 400 at or near the distal end of corewire 400. If corewire 400 is pulled in a distal direction relative to overtube 398, struts 418, 420 and cylindrical section struts 424, 426 flare outward at their attachment to cylindrical section 422 as cylindrical section 422 extends outward from overtube 398 to assume a deployed configuration, as shown in FIG. 8B. In the deployed configuration, fiber based filter matrix 416 extends across the lumen of the vessel to filter flow passing the filter. Filter matrix 416 can comprise a mat of fibers, such as SCF fibers, and fibers can be attached, for example, with adhesive, heat bonding, mechanical clamping or combinations thereof. Struts 408, 410, 418, 420, 424, 426 may be formed, for example, from metal or metal alloy, such as stainless steel or Nitinol®, or other suitable biocompatible material and may be welded, soldered, clamped, combinations thereof or otherwise suitably attached to appropriate structures.

FIG. 8A shows filters 404, 406 in a low profile delivery configuration. If corewire is moved in a proximal direction relative to overtube 398, filters 394, 396 transition simultaneously to a deployed configuration as shown in FIG. 8B. In particular, contracting section 402 compresses, and struts 408, 410, 418, 420, 424, 426 bend as cylindrical sections 412, 422 transition to an extended configuration. In the deployed configuration, cylindrical sections 412, 422 generally contact the walls of the vessel such that flow past the filters passes through filter matrices 406, 416, respectively. If corewire 400 is moved in a distal direction relative to overtube 398, filters 394, 396 at least partially collapse to a lower profile configuration relative to the deployed configuration in FIG. 8B. The collapsed configuration of filters 394, 396 may not return to the original configuration in FIG. 8A since changes in the materials upon deployment may not be fully reversible.

Figure 8C:
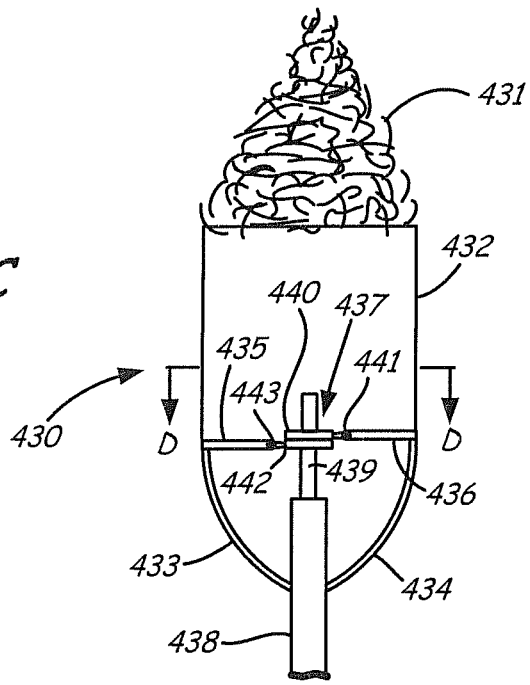
FIG. 8C is a side view of alternative embodiments of a distal filter element for incorporation in a filter device similar to the device in FIGS. 8A and 8B.

As shown in 8A and 8B, corewire 400 is fixedly attached to cylindrical section struts 424, 426. In alternative embodiments, cylindrical section struts can be attached to a detachable support that grips the corewire. In some embodiments, the structure providing the disengagement can be irreversible such that the corewire does not re-engage the filter element when the corewire is moved in a distal direction relative to the overtube. Referring to FIG. 8C, a filter element 430 replaces filter element 396 of FIG. 8B. Filter element 430 comprises mesh filter 431, cylindrical section 432, lower struts 433, 434, upper struts 435, 436 and detachable support 437. Lower struts 433, 434 connect cylindrical section 432 with overtube 438. Detachable support 437 connects upper struts 435, 436 with corewire 439. Detachable support 437 comprises first ring 440, first hinge 441, second ring 442 and second hinge 443. Rings 440, 442 can comprise rubber or other elastic material that grips corewire 439 under moderate force, but releases corewire 439 under greater force.

Figure 8D:
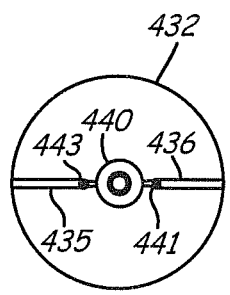
FIG. 8D is a sectional view of the filter element of FIG. 8C taken along line D-D of FIG. 8C.
Figure 8E:
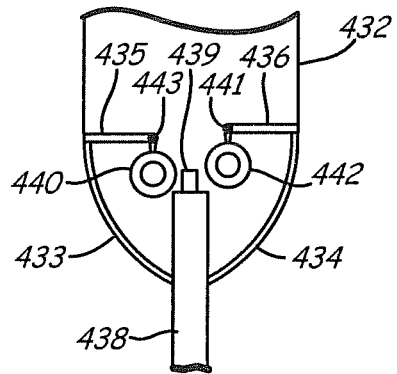
FIG. 8E is a fragmentary side view of the filter element of FIG. 8C in which a corewire has disengaged from a detachable element.

Based on the design of detachable support 437, if corewire 439 is laterally moved in a proximal direction relative to overtube 438, detachable support 437 grips corewire 439 to deploy the filter until cylindrical section 432 contacts a vessel wall such that struts 435, 436 cannot bend further. The extended configuration of filter element 430 with an attached corewire 439 is shown in FIG. 8C. The sectional view of FIG. 8D shows the extended upper struts 435, 436 with rings 440, 442 engaging corewire 439. With the struts in a constrained configuration, further force on the corewire in a proximal direction relative to the overtube can disengage the corewire from rings 440, 442. Referring to FIG. 8E, when corewire 439 disengages from rings 440, 442, hinges 441, 443 allow for the movement of rings 440, 442 relative to struts 435, 436 so that corewire 439 does not re-engage rings 440, 442 if corewire 439 is advanced in a distal direction.

Figure 9A:
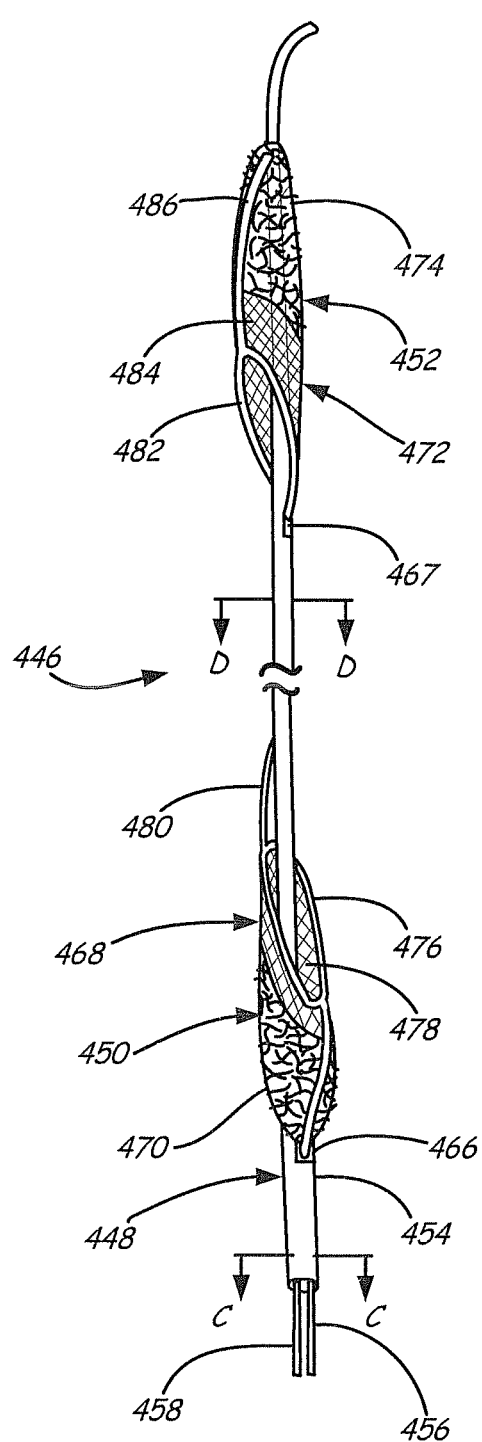
FIG. 9A is a side view of a filter device having a distal filter and a proximal filter along a single integrated guiding device with two corewires that provide for the independent deployment and collapse of the distal filter element and the proximal filter element, in which the filter elements are shown in a low profile delivery configuration.
Figure 9B:
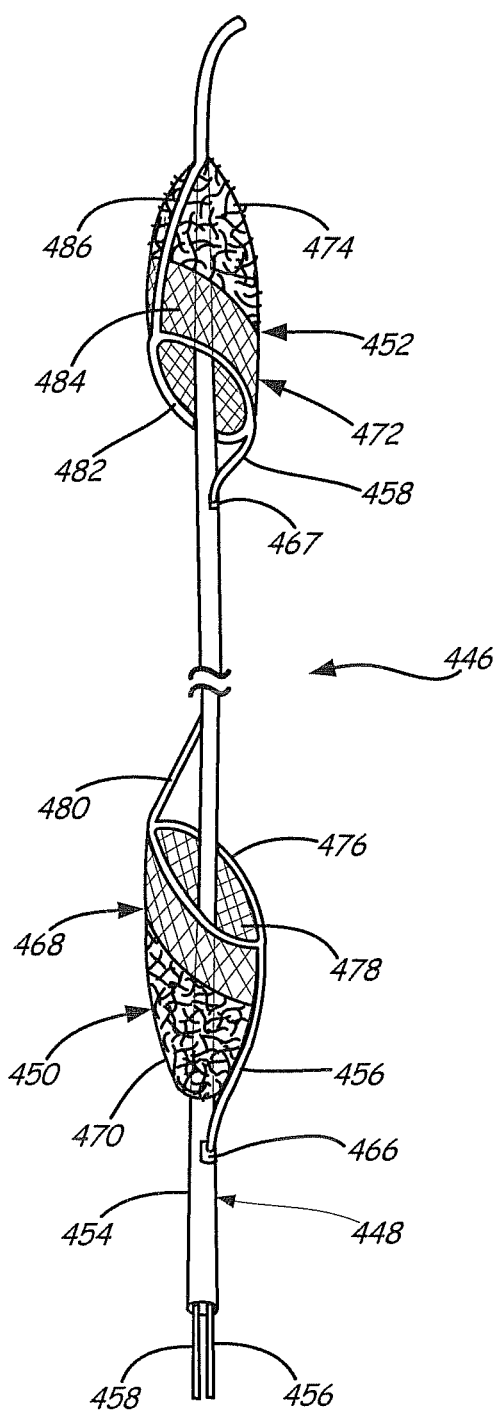
FIG. 9B is a side view of the filter device of FIG. 9A in which the filter elements are shown in an extended, deployed configuration.
Figure 9C:
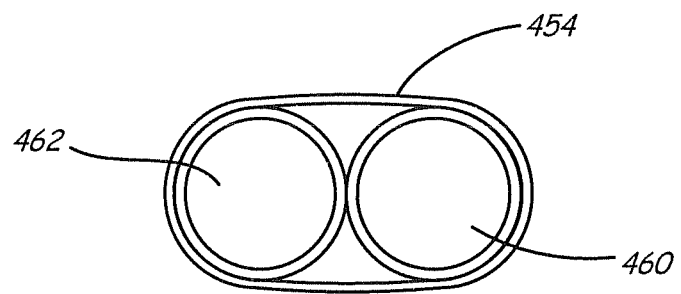
FIG. 9C is a sectional view of the integrated guide structure of FIG. 9A taken along line C-C.
Figure 9D:
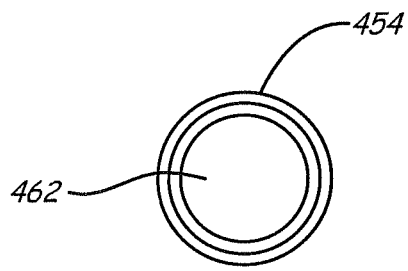
FIG. 9D is a sectional view of the integrated guide structure of FIG. 9A taken along line D-D.

Another filter device is illustrated in FIGS. 9A and 9B having two filter elements attached to a common integrated guide structure. In the filter device of FIGS. 9A and 9B, two separate corewires provide for independent actuation of the two filter elements. Specifically, referring to FIGS. 9A and 9B, a filter device 446 comprises an integrated guide structure 448, proximal filter element 450 and distal filter element 452. Integrated guide structure 448 comprises an overtube 454 and independent corewires 458 and 460. Overtube 454 comprises lumens 462, 464, as illustrated in a section view of FIG. 9C, as well as ports 466, 467 that are distal openings of lumens 462, 464, respectively. At least a portion of corewire 456 is within lumen 462 and extends from port 466 of overtube 454. Similarly, at least a portion of corewire 458 is within lumen 464 and extends from port 467 of overtube 454. Generally, corewires 456, 458 also extend from the proximal end of overtube 454 such that the proximal ends of corewires 456, 458 can be used to manipulate independently the relative positions of corewires 456, 458 and overtube 454. Corewires 456, 458 and overtube 454 can independently comprise one or more torque couplers to restrain the angular motion of corewires 456, 458 within lumens 460, 462 and/or to limit the longitudinal motion of the corewires relative to the overtube.

Filter element 450 comprises a basket filter 468 and a fiber based matrix filter 470 connected to the basket filter. Similarly, filter element 452 comprises a basket filter 472 and a fiber based matrix filter 474 connected to basket filter 468. Basket filter 468 comprises a hoop 476, a woven mesh 478 extending from hoop 476 and a strut 480. Strut 480 connects hoop 476 to overtube 454 in a distal direction relative to woven mesh 478. Hoop 476 is connected to corewire 456 at a position displaced from the location of the connection to strut 480 to apply appropriate torque to hoop 476 to transition the filter between configurations. FIG. 9A shows filter element 450 in a lower profile configuration. If corewire 456 is moved in a distal direction relative to overtube 454, hoop 476 transitions to a deployed configuration, and strut 480 flexes to support hoop in the deployed configuration. Woven mesh 478 connects to hoop 476 at one end and to overtube 454 at the other end such that all flow through hoop 476 passes through woven mesh 478.

Basket filter 472 comprises a hoop 482, a woven mesh 484 extending from hoop 482 and a strut 486. Strut 486 connects hoop 482 to overtube 454 in a distal direction relative to woven mesh 484. Strut 486 extends along woven mesh 484. Hoop 482 is connected to corewire 458 at a position displaced from the location of the connection to strut 486 to provide for suitable torque on hoop 482 to transition the filter between configurations. FIG. 9A shows filter element 452 in a lower profile configuration. If corewire 458 is moved in a distal direction relative to overtube 454, hoop 482 transitions to a deployed configuration, and strut 486 flexes to support hoop in the deployed configuration. Woven mesh 484 connects to hoop 482 at one end and to overtube 454 at the other end such that all flow through hoop 482 passes through woven mesh 484. The opening to woven mesh 484 through hoop 482 is oriented in a proximal to distal direction relative to overtube 454 while the opening to woven mesh 484 through hoop 482 is oriented in a distal to proximal direction relative to overtube 454. These orientations of filter elements 450, 452 are consistent for placement respectively in the brachiocephalic artery and left carotid artery with the guide structure extending form the right subclavian artery. Suitable materials for the respective elements are described above in the context of similar elements in different embodiments. Also, the respective elements can be similarly attached as described above for the selected material.

As noted above, filter elements 450, 452 can be independently deployed and/or collapsed. As shown in FIG. 9A, filter elements 450, 452 are shown in a lower profile delivery configuration. As desired for deployment, corewires 456, 458 can be moved independently in a distal direction relative to overtube 454 to respectively deploy filter elements 450, 452. Similarly, corewires 456, 458 can be moved independently in a proximal direction relative to overtube 454 to collapse respectively filter elements 450, 452 for removal from the patient.

3. A Single Filter Structure to Span Arteries Along the Aortic Arch

A single filter structure can be designed to span between arteries branching from the aorta along the aortic arch so as to provide simultaneous filtration of blood flow into the left carotid artery and the right carotid artery. Such a filter structure may comprise a single filter element that spans the aortic arch between the brachiocephalic and left carotid arteries. Alternatively, such a structure may comprise multiple filter elements attached to a single support structure that spans the aortic arch when deployed. The filtration of flow into the brachiocephalic artery correspondingly filters flow to the right carotid artery, which branches from the brachiocephalic artery.

Figure 10:
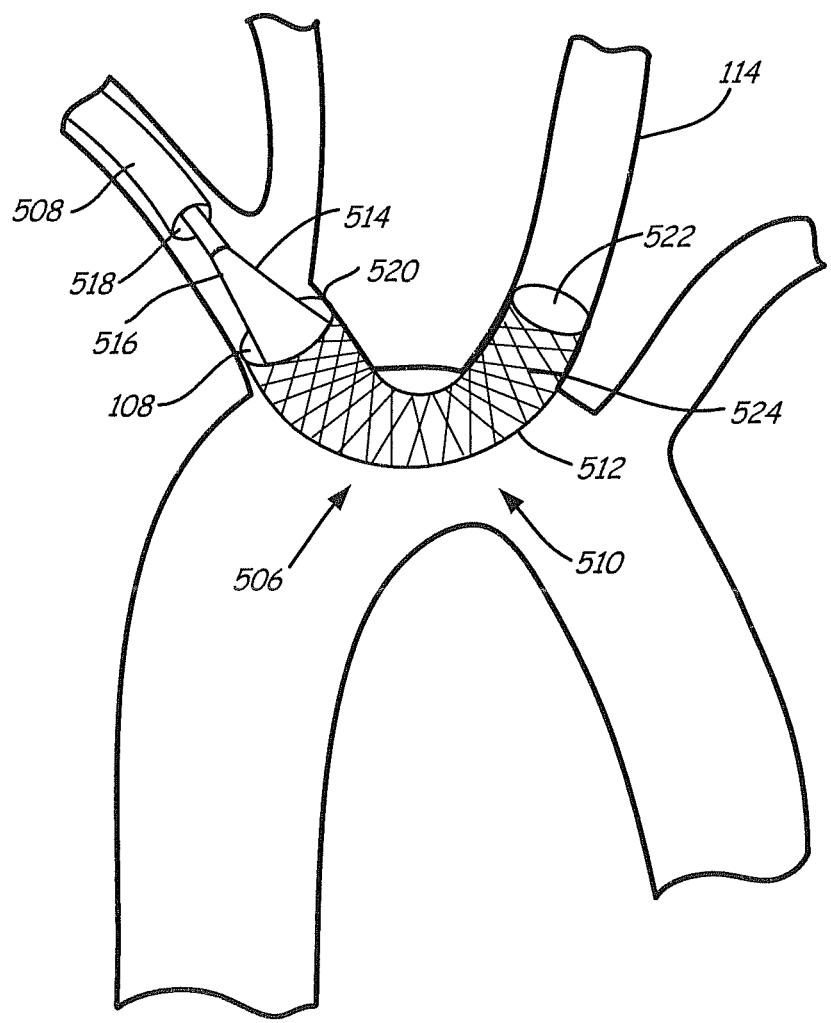
FIG. 10 is a sectional view of the aortic arch depicting a filter system with a single filter element spanning between the left carotid artery and the brachiocephalic artery.

FIG. 10 illustrates an embodiment of a filtration system 506 comprising a catheter 508 and filter device 510 designed to span between the brachiocephalic artery and the left common carotid artery. Filter device 510 comprises a filter element 512 and tethers 514, 516. Tethers 514, 516 can extend through lumen 518 of catheter 508. Filter element 512 comprises a proximal hoop 520, a distal hoop 522 and filter membrane 524. Proximal hoop 520 generally is connected to tethers 514, 516. In general, one tether, three tethers or more than three tethers can be used as an alternative to two tethers. Hoops 522, 524 can comprise a resilient material such that the hoops can be placed in a lower profile configuration for delivery. The hoops material can be self-extending such that the hoops extend to a deployed configuration when released in the vessel, such as being removed from a sheath, catheter of the like. Tethers 514, 516 and filter element 512 may be formed from suitable materials as described above. In its deployed configuration, filter element 512 can be dimensioned so that its distal and proximal ends extend at least partially into left common carotid artery 114 and brachiocephalic artery 108, respectively.

Figure 11A:
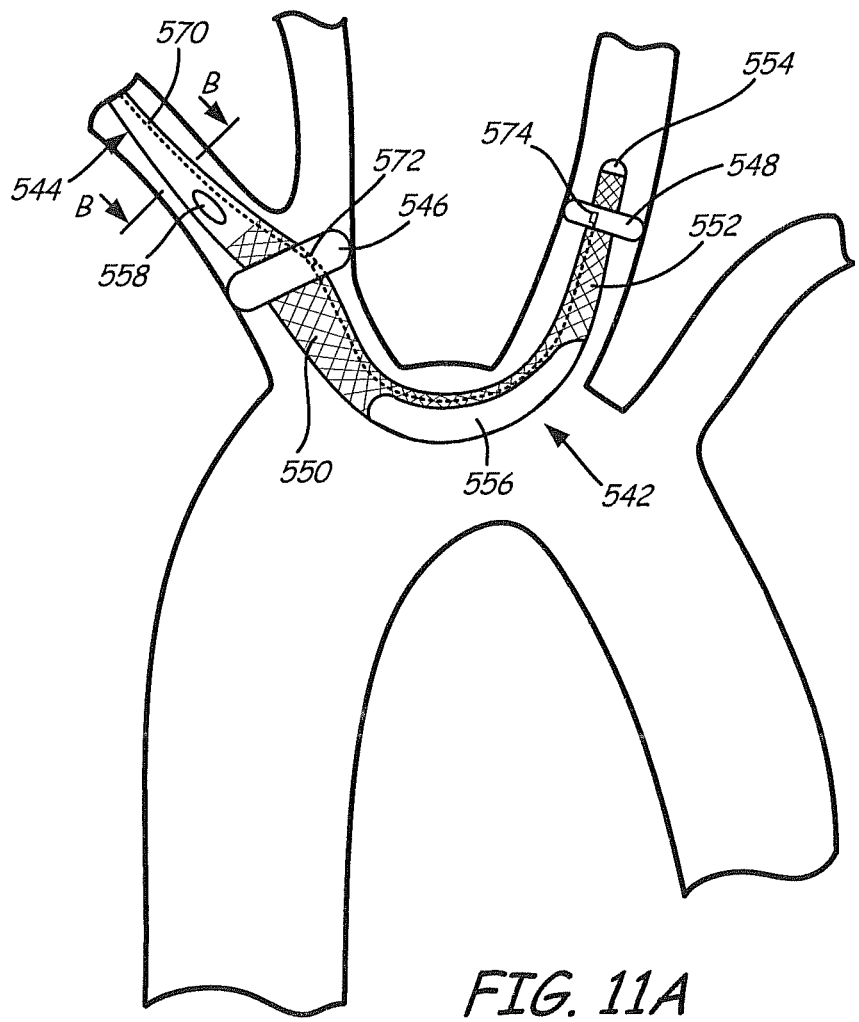
FIG. 11A is a sectional view of the aortic arch depicting a filtration device spanning between the left carotid artery and the brachiocephalic artery in which the filtration device comprises two occlusive elements, two internal filters and ports to provide filtered flow past the occlusive elements into the left carotid artery and the brachiocephalic artery.

Referring to FIG. 11A, in a further embodiment, a filter device 542 comprises tubular element 544, proximal occlusive element 546, distal occlusive element 548, proximal filter element 550, and distal filter element 552. Tubular element 544 comprises a distal port 554, a central port 556 and a proximal flow port 558. In this embodiment, occlusive elements 546, 548 can be attached to the exterior of tubular element 544 at suitable positions so that occlusive elements 546, 548 can be deployed in brachiocephalic artery 108 and left common carotid artery 114, respectively.

Figure 11B:
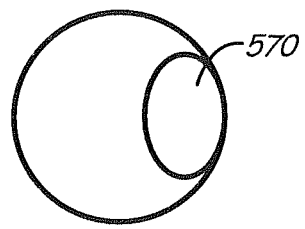
FIG. 11B is a sectional view of the filtration device of FIG. 11A taken along line B-B of FIG. 11A.

Occlusive elements 546, 548 can be balloons, although other occlusive elements can be used, such as non-porous polymer membranes on a self expanding metal frame that can be released from a sheath or the like. If occlusive elements 546, 548 comprise balloons, tubular element 544 generally comprises one or more inflation lumens. If a single inflation lumen is used, occlusive elements 546, 548 are simultaneously inflated when an inflation fluid, such as sterile saline is directed into the inflation lumen. An inflation lumen 570 is shown in phantom lines in FIG. 11A and in the sectional view in FIG. 11B. Inflation lumen 570 is in fluid communication with occlusive elements 546, 548 through inflation ports 572, 574, respectively. If a plurality of inflation lumen is used, occlusive elements 546, 548 can be independently inflated.

Proximal filter element 550 is positioned within tubular element 544 between proximal flow port 558 and central port 556 such that flow into central port 556 is filtered prior to exiting proximal flow port 558. Similarly, distal filter element 552 is positioned within tubular element 544 between central port 556 and distal port 554. Filter elements 550, 552 can be similar to filter element 218 of FIG. 3B. A separate guide lumen can be used to provide for placement of the catheter in a desired location. Such a separate guide lumen can be placed, for example, along the side of the catheter tubular element. In this way, a guide structure can be used for deployment without interfering with the filter elements.

4. Catheter With an Exterior Filter to Filter Flow in the Aorta

In further embodiments, a filter can be delivered into the aorta to filter blood flow from the ascending aorta into the aortic arch. For example, the filter can be delivered into the ascending aorta from the descending aorta by way of a femoral artery, although other approaches can be used, such as from the left subclavian artery into the ascending aorta. To maintain access to the heart through the aorta, the filter can be mounted on the exterior of a catheter such that treatment instruments for the heart can be introduced through the catheter. Through the placement of a filter in the ascending aorta, blood is filtered not only for the carotid arteries but also for the peripheral arteries.

Figure 12:
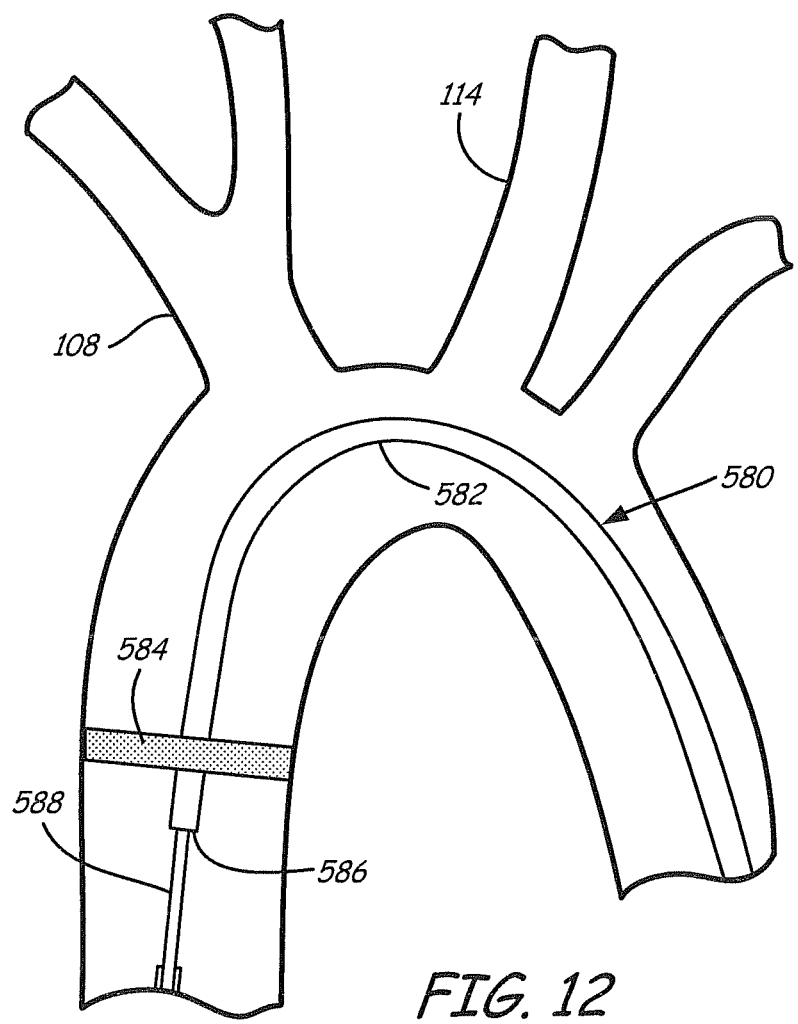
FIG. 12 is a sectional view of the aortic arch depicting a catheter extending into the ascending aorta from the descending aorta with an external filter element on the exterior of the catheter filtering flow within the ascending aorta.

Referring to FIG. 12, filtration catheter 580 comprises a tubular structure 582 and a filter element 584. Tubular structure 582 has a distal port 586. Heart treatment tool 588 is shown extending from distal port 590 to access the heart through the ascending aorta. Catheters with externally mounted filters are described above in the context of FIG. 3A and FIG. 7. These catheters with external filter can be used in the context of the placement in FIG. 12 with appropriate sizing of the catheter and filter.

Procedures for Embolic Protection During Heart Procedures

The filtration systems described herein can be effectively used for embolic protection during and/or following procedures on the heart. In particular, the filtration systems described herein can be used to provide embolic protection during endovascular cardiac procedures performed in or around the left atrium and left ventricle of the heart, although the filter may also be useful for procedures on the heart with an approach through the patient's chest. Some procedures may involve an endovascular approach to the heart to accomplish certain steps of the procedure and less invasive approaches through the patient's chest for other aspects of the procedure, such as providing cardiopulmonary bypass. The procedures on the heart can result in emboli that can flow from the aorta and then for circulation to other parts of the body. While emboli can be undesirable in any vessel, the circulation of emboli into the carotid arteries, and in particular the internal carotid arteries, can result in the flow to the patient's brain where the emboli can cause strokes or other adverse consequences. Therefore, it is very desirable to filter emboli from the flow into the internal carotid arteries.

Thus, in some embodiments, filter elements may be positioned, for example, in the ascending aorta such that emboli are reduced or eliminated from circulating to other parts of the body from the aorta. Additionally or alternatively, filter elements can be placed so that emboli are removed from flow into the carotid arteries without removing emboli from flow through the descending aorta and/or one or both of the subclavian arteries where emboli generally may not present a significant concern. When the risk for emboli formation is reduced or eliminated, filter elements may be safely withdrawn from the patient in such a way as to restrict emboli captured by the filter from entering the blood flow into the carotid arteries.

Emboli can be released into the blood flow from various procedures on the heart. In particular, heart valve replacement involves significant manipulations of the heart tissue and can be associated with a risk of emboli generation. Other heart procedures include, for example, heart valve repair procedures. Emboli that are generated within or near the left heart chambers may be released into the aorta upon resumption of heart pumping if cardiopulmonary bypass is used. Emboli released into the ascending aorta can flow downstream and may generate a risk of emboli within the carotid arteries. In some embodiments, heart procedures of interest include, for example, endovascular procedures in which instruments are delivered in a percutaneous format up an artery, such as the femoral artery or a subclavian artery to reach the heart.

While the filtering procedures described herein are applicable for protection during various heart procedures, the procedures can be advantageously used in conjunction with performing percutaneous heart valve replacement. Generally, a percutaneous procedure to replace the aortic valve comprises delivery of a prosthetic heart valve through a patient's peripheral vasculature to an area at or near the valve root, such as the aortic annulus or the mitral valve annulus. The valve replacement procedure may comprise the excising of the native valve, although in some embodiments, the replacement valve can be placed within the native valve without removing the native valve. The patient may be placed on cardiopulmonary bypass to provide for oxygenated blood flow while the valve is being replaced. The prosthetic heart valve can be delivered as a single unit or it can be delivered as a plurality of sub-units and assembled in the patient's body. The procedure further comprises implantation of the prosthesis in the desired location. Where the prosthesis comprises a plurality of sub-units, the components of the prosthetic valve can be assembled prior to implantation and/or assembled within the patient.

An exemplary method for performing such a percutaneous valve replacement procedure comprises the delivery of a compressible prosthetic aortic valve comprising a tissue engaging base, designed to hold the prosthesis in place at or near the annulus of the native valve, and a leaflet element, designed to function as a valve. The prosthesis can comprise a plastically deformable structure that is designed to retain its configuration when crimped for delivery. The prosthesis can be affixed to a delivery catheter comprising, concentrically, an outer sheath, an optional push catheter, and a balloon catheter, and the prosthesis can be attached to the balloon catheter such that when the balloon is inflated, the prosthesis adopts its expanded configuration. The catheter can be tracked into the region of the valve annulus from a variety of peripheral arteries or veins, for example, the left femoral artery or right femoral artery. The outer sheath can be tracked into the ascending aorta from a peripheral artery, for example, using a variety of standard techniques such as with the use of a guidewire. When the prosthesis reaches the desired location within the aortic annulus, the outer sheath is pulled back, exposing the prosthetic valve element. In appropriate embodiments, the balloon is then expanded, placing the prosthesis in its expanded configuration. The balloon is then deflated and the delivery structure removed. For alternative embodiments in which the prosthesis has a self-expanding design, simply removing the prosthesis from the outer sheath can induce an expanded configuration. Further discussion on this heart valve replacement procedure as well as alternative embodiments can be found in U.S. Pat. No. 6,454,799 to Schreck, entitled "Minimally-Invasive Heart Valves and Methods of Use," incorporated herein by reference. Heart valve prostheses that can be placed in an aortic valve position or mitral valve positions with our without removing the native valve are described further in U.S. Pat. No. 7,329,278 to Seguin et al., entitled "Prosthetic Valve for Transluminal Delivery," incorporated herein by reference.

The filtration systems described herein can be used to provide embolic protection for selected vessels during a particular heart procedure. The filters are generally guided into position through a selected artery. The various filtration system designs described above are generally designed for delivery through a femoral artery or through one of the subclavian arteries to access portions of the vessels that provide flow to the carotid arteries. The suitability of a particular artery for the delivery of a filter can be evaluated with reference to considerations, such as the vessels to be provided with embolic protection, the particular heart procedure being performed and the specific design of the filtration system being deployed. One or more guide catheters can be positioned to facilitate the delivery and/or removal of the filters, and the guide catheters may or may not remain in place during the time that the filters are within the patient's vessels. In general, the filters and the associated structures should be designed appropriately to avoid interfering with any tools used to perform the heart procedure. For embodiments of the filtration system involving the placement of a plurality of filters, the vessel or vessels selected for the introduction of the filters generally provide for the tracking of the respective filter elements to the desired locations sequentially or simultaneously for appropriate timing for the placement of the filters.

In general, the filters can be deployed at a selected time, which generally is prior to the time at which there is a significant risk for emboli generation. The appropriate timing for deployment of the filter(s) generally depends significantly on the nature of the heart procedure. In some embodiments, if the filters do not interfere with any of the heart procedure steps or instruments, the filters can be deployed prior to any significant portions of the heart procedure. If good flow is maintained across the filters during the whole procedure, the filters can be left in place for a significant period of time without any adverse effects. In some embodiments, some steps of the heart procedure may be performed prior to the placement of one or more filters. It may be advantageous to deploy the filters at a later stage if the early steps of the heart procedure do not generate a significant embolic risk and/or if the early steps of the heart procedure could determine that the continuation of the heart procedure is contraindicated. The filters though are generally deployed prior to any significant risk of emboli generation within the aorta.

After the significant risk for emboli generation has passed, the filtration systems can be removed from the patient. In some embodiments, the filtration system can be removed after the heart procedure has completed. It may be desirable to continue filtration until after cardiopulmonary bypass has been ended and the natural heart function has been restored for a period of time. If some steps of heart procedure do not generate a significant risk from emboli or if the filter may interfere with some steps of the heart procedure, the filters may be removed prior to completing all of the steps of the heart procedure. If some portions of the filtration system are not needed at some stage of the procedure while other portions of the filtration system are desired, a portion of the filtration system maybe removed while another portion of the system can be kept in a deployed configuration. Furthermore, the filters can be removed partially or completely at one stage in the procedure and replaced with the same and/or different filters at a later stage of the procedure.

Generally, to effectuate the removal of the filtration system from the patient, the one or more filters can be collapsed to a recovery configuration and removed from the vessel. The steps to accomplish these objectives depend significantly on the design of the filter(s). For example, some filters comprise an actuating component that can be used to transition the filter to a lower profile recovery configuration. In some embodiments, a filter may be collapsed with a sheath or the like that is contacted with the proximal portion of the filter to mechanically collapse the filter, which may or may not also involve the withdrawal of the filter partially or completely into the end of the sheath. In some embodiments, it may be desirable to drag the filter in an expanded configuration over a portion of the vessel prior to removal of the filter. For example, a filter in the left common carotid artery can be dragged near the opening into the aorta where any emboli along the surface of the filter may be washed down the descending aorta where the emboli can generally be reasonably tolerated to reduce the risk of emboli being released into the carotid artery during removal of the filter.

In some embodiments, suction may be applied during some portion of the process to remove a filter from the vessel. If suction is applied, the tip of an aspiration catheter may be positioned near the filter and aspiration can be applied during the collapse of the filter to a lower profile configuration. The filter may be brought into the tip of the aspiration catheter, and the aspiration may be continued while the filter is brought into the tip of the aspiration catheter. The application of suction can be particularly desirable for filters with three dimensional filtration matrices. The use of suction for the recovery of a filter device is discussed further in published U.S. patent application 2007/060944A to Boldenow et al., entitled "Tracking Aspiration Catheter," and published U.S. patent application 2005/0277976 to Galdonik et al., entitled "Emboli Filter Export System," both of which are incorporated herein by reference.

In additional embodiments, it may be desirable to slide the device out from the carotid arteries. Upon exiting of the edge of the device, any emboli along the surface of the device can be carried downstream from the opening of the carotid arties into vessels where the emboli will not create any significant concerns. This can be particularly useful for embodiments involving an occlusion device or for embodiments in which the design does not readily allow the placement of an aspiration catheter adjacent the device.

The procedures described herein generally involve access to the patient's vascular system through a small hole. Generally, the selected vessel can be accessed, for example, with conventional tools, such as introducers, cannula and the like. Hemostatic valves, leur fittings, other fittings and the like can be used to reduce bleeding from the patient during the procedure. The fittings provide for the introduction and removal of various devices at appropriate times in the procedure.

1. Individual Filter Elements for Common Carotid Artery Filtering

As described above in the context of FIGS. 1-5, filtration systems within this group provide embolic protection to the left carotid artery and right carotid artery using separate filtration devices. The filtration devices can comprise a guide structure and a single filter element or filter elements to be deployed un-tethered. A method for providing embolic protection with such protection systems comprises deployment and recovery of such systems. Deployment of such systems generally comprises delivery of a filtration device to the right carotid artery or the brachiocephalic artery and deployment of the filter element in an extended configuration. Deployment of the filtration system generally further comprises delivery of a filtration device to the left carotid artery and deployment of the filter element in an extended configuration. Recovery of such systems generally comprises placing deployed filter elements in a recovery configuration and withdrawing the filtration system from a patient's body generally without significant release of emboli are not released into the carotid arteries.

Referring to FIG. 2A, guide catheter 130 can optionally be used to facilitate the subsequent delivery of filtration devices. The guide catheter can be positioned, for example, using conventional techniques. Specifically, as implied in FIG. 2A, deployment of the filtration devices comprises introduction of guide catheter 130 into a patient and tracking the distal end of the guide catheter into the right subclavian artery. Filter devices 132, 134 can then be delivered through the guide catheter sequentially or simultaneously. The distal ends of filter devices 132, 134 are tracked respectively to the right carotid artery and the left carotid artery. Once the filter elements are at their desired positions, the filter elements can be deployed. The deployment of the filters depends on the design of the filters. For example, self-extending filters can be deployed through the withdrawal of a covering sheath such that the filters can extend to their deployed configuration. In other embodiments, the filter elements can be actuated to their deployed, extended configuration. For example, the filter of FIGS. 6A and 6B can be actuated by pulling the corewire in a proximal direction relative to the overtube. As shown in FIG. 2A, filter element 140 is delivered within the right common carotid artery, and filter element 144 is delivered into the left common carotid artery, although either filter can be alternatively delivered into the corresponding internal carotid artery.

Recovery of the filtration system illustrated in FIG. 2A comprises placing filter elements 140, 144 into a recovery configuration and withdrawing filter devices 132 and 134 from the patient's body through catheter 130. In some embodiments, filter device 132 and/or filter device 134 can be de-actuated to place the filter in a recovery configuration. For example, the filter device of FIGS. 6A and 6B can be de-actuated by pushing the corewire in a distal direction relative to the overtube. Where aspiration is desirable for either filter element 140,144, catheter 130 can be removed from a patient's body and an aspiration catheter can be delivered to either filter element 140, 144 over guide structures 138, 142, respectively. Alternatively, if guide catheter 130 has a large enough diameter, aspiration catheters can be tracked through the guide catheter. For self-extending filter elements, a catheter can be brought up to the filters to mechanically collapse the filters, and these retrieval catheters can be brought up to the filters similarly as the aspiration catheters.

With the filtration system illustrated in FIG. 2B, similar methods can be used as the methods described above for the filtration system in FIG. 2A. Referring to FIG. 2b, deployment of the filtration system comprises delivery of guide catheters 152, 154 into the right subclavian artery and left subclavian artery, respectively. Subsequently, filter devices 148, 150 are tracked into the right common carotid artery and the left common carotid artery, respectively. The deployment of the filters and recovery of the filters can be performed as previously described for the system in FIG. 2A. The filtration system in FIG. 2B avoids any possible interference associated with the use of a common guide structure, but the methods for the deployment of the filtration system in FIG. 2B involve two entry points into the patient for filter delivery in contrast with the single entry point used for the filtration system of FIG. 2A.

With respect to the procedures relating to the filtration systems in FIGS. 3A and 3B, catheters 190 or 206 replace first filter device 132. Filter devices 188 (FIG. 3A), 204 (FIG. 3B) can be delivered into the left carotid artery similar to the delivery of filter device 132 (FIG. 2A), and the deployment and retrieval of filter devices 188, 204 can also be similar to the corresponding steps for filter device 132. Referring to FIG. 3A, catheter 190 generally can be put in place prior to or after the placement of filter device 188. Similarly, filter element generally 200 can be deployed prior to or after the deployment of filter element 194. If filter element 194 is a self-expanding filter, catheter 190 can be put in place after the deployment of filter element 194 if catheter 190 has the potential of interfering with the deployment of filter 194. With respect to the order of retrieval of the filters, catheter 190 and filter device 188 can be retrieved in either order if no additional structured are used in the process. If a suction catheter or other catheter is used in the retrieval of filter element 194, filter element 200 can be collapsed first to allow for the removal of catheter 190 or for the use of catheter 190 to facilitate the retrieval of filter 194 by advancing catheter 190 to filter 194. Filtration system 202 in FIG. 3B can be manipulated similarly to filter system 186 in FIG. 3A with the appropriate deployment and collapse of occlusive element 216 substituted the deployment and collapse of filter element 200.

With respect to filtration system 242 shown in FIG. 4, catheter 244 and filter device 248 generally can be delivered in either order. However, catheter 244 is delivered with its distal end in the brachiocephalic artery prior to the delivery of filter device 246 since the delivery of filter device 246 is effectuated through a port of catheter 244. Similarly, catheter 244 can remain in a deployed position while filter device 246 is retrieved. Catheter 244 and filter device 248 generally can be removed from the patient in either order or simultaneously.

Referring to FIG. 5, filters 284, 286 generally are deployed with a suitable delivery tool and removed with a corresponding removal tool. The delivery tool may or may not be the same as the removal tool. Suitable delivery tools and removal tools are described above. In general, the filters can be delivered and retrieved independently, and the delivery and removal of filters 284 and 286 generally can be selected to be in any order. The delivery and removal tools generally can be tracked to the desired locations through any peripheral artery, such as a subclavian artery or a femoral artery.

2. A Plurality of Filter Elements on a Common Guide Structure

In some embodiments, a filtration system is deployed system for filtering flow to the carotid arteries that has a plurality of filter elements on a common guide structure. The method involving the use of these filter devices generally comprises deployment and recovery of the protection system in which the device scans a section of the aortic arch between the left carotid artery and the brachiocephalic artery. The filter devices comprise a guide structure, a proximal filter element attached to the guide structure, and a distal filter element attached to the guide structure. The guide structure can be an integrated guiding device with one or more corewires within an overtube to facilitate delivery and/or collapse of the device. Generally, the filter device is tracked through the right subclavian artery into the brachiocephalic artery and to the left common carotid artery so that the proximal filter element filters flow to the right carotid artery and the distal filter element filters flow to the left carotid artery. Subsequently, the filter elements can be simultaneously or sequentially placed into a deployed configuration. Recovery of a filtration system with two filters on a guide structure generally comprises sequentially or simultaneously placing the filter elements in a recovery configuration, which can depend on the design of the filters. The protection device is subsequently removed from a patient. In some embodiments of the method, placing any or all of the filter elements in a recovery configuration and/or removing a protection device can be done under aspiration.

Figure 13A:
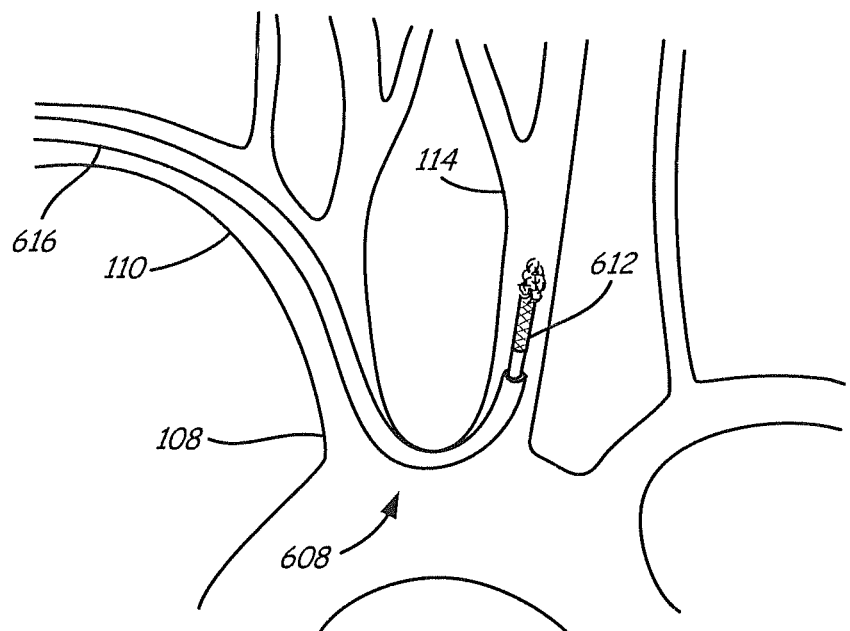
FIG. 13A is a sectional view of the aortic arch depicting a filtration device extending from the right subclavian artery into the left carotid artery in which the filter elements are in a low profile delivery configuration.
Figure 13B:
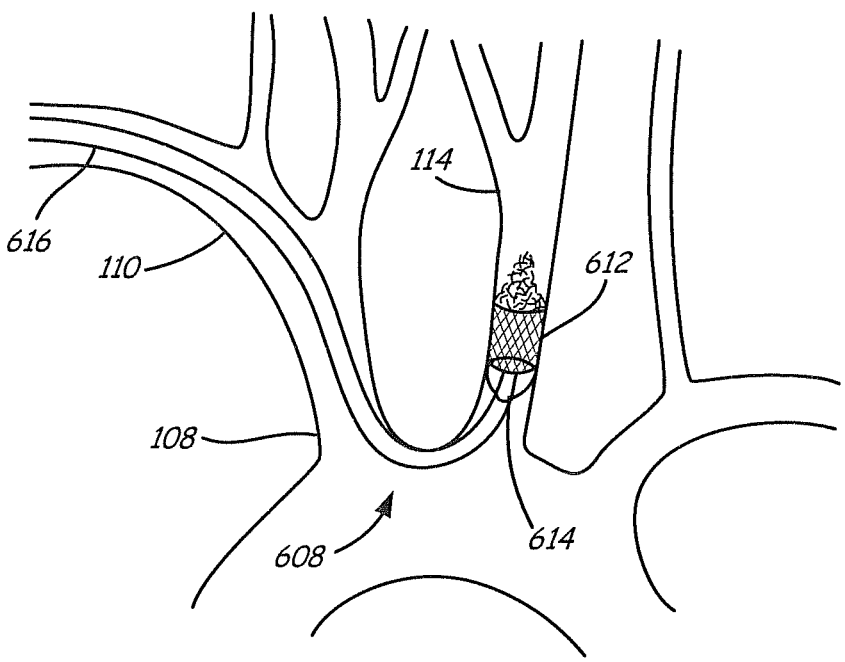
FIG. 13B is a section view of the aortic arch depicting the filtration device of FIG. 13A in which a distal filter element is in a deployed extended configuration.
Figure 13C:
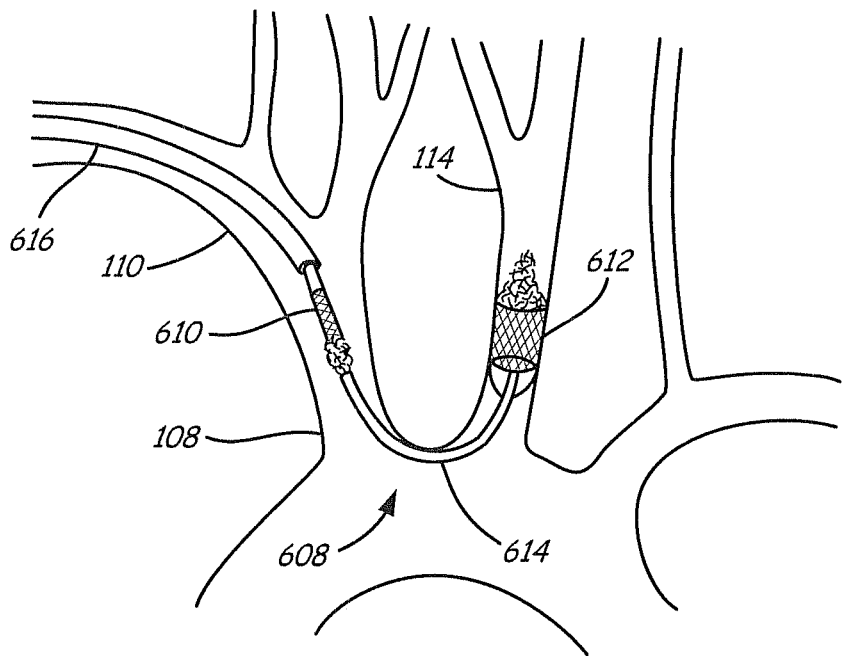
FIG. 13C is a sectional view of the aortic arch depicting the filtration device of FIG. 13A in which the distal filter element is deployed and a proximal filter element is exposed in a low profile configuration through the withdrawal of a sheath.
Figure 13D:
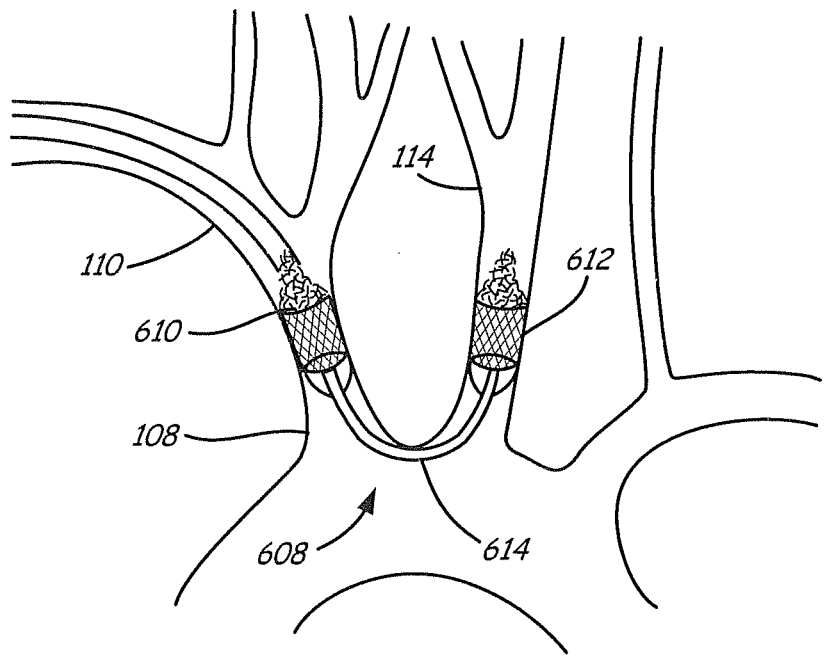
FIG. 13D is a sectional view of the aortic arch depicting the filtration device of FIG. 13A in which the distal filter element is deployed and the proximal filter element is deployed in an extended configuration.

FIGS. 13A-D illustrates a method for providing embolic protection using a filter system comprising a plurality of filter elements on a common guide structure. The methods for using these filter devices can be applicable for the filter devices in FIGS. 8 and 9. Thus, in some embodiments, the guide structure can comprise an inner core(s) that actuate filter element(s) either sequentially or simultaneously between a delivery and deployed configuration. In other embodiments, the filter elements can comprise self-expanding structures that adopt a deployed configuration when a constraint is removed. Referring to FIG. 13D, elements of a filter device 608 comprises a proximal filter element 610, a distal filter element 613, and a guide structure 614.

Referring to FIG. 13A, the method of using filter device 608 comprises delivery of a delivery catheter 616 through the right subclavian artery and into the left common carotid artery such that distal filter element is within the left carotid artery. Subsequently, protection device 608 is tracked through delivery catheter 616 so that filter element 612 extends completely from delivery catheter 616 and is positioned in a desirable location. Where filter element 612 comprises a structure that does not spontaneously assume a deployed configuration when extended completely through delivery catheter 616, filter element 612 is then actuated into a deployed configuration, as shown in FIG. 13B. Referring to FIGS. 13C, delivery catheter 616 is then moved proximally with respect to filter element 612 until filter element 610 extends complete from delivery catheter 616. Where filter element 610 comprises a structure that does not spontaneously assume a deployed configuration when extended completely from delivery catheter 616, filter element 612 is then actuated into a deployed configuration, as shown in FIG. 13D. Then, catheter 616 and be left in place, withdrawn further, or completely withdrawn from the patient's body.

An appropriate embodiment of a recovery method varies with the type of filter element deployed. Generally, a recovery method comprises placing proximal filter element 610 and distal filter element 612 into respective recovery configurations. If filter element 610 is self-expanding, an external constraint can be introduced to mechanically transition filter element 610 into a recovery configuration. For example, delivery catheter 616 or an introduced aspiration catheter can be used as such a constraint. Furthermore, if filter element 612 comprises a self-expanding structure, an external constraint, such as delivery catheter 616 or a separate catheter, can be introduced to mechanically transition distal filter element 612 into a recovery configuration. In further embodiments, an actuation element, such as a corewire, can be used to transition the filter elements into a lower profile recovery configuration. In general, the proximal filter element 610 and distal filter element 612 can be sequentially or simultaneously transitioned into a recovery configuration. Filter device 608 can be withdrawn through catheter 616 or separate from catheter 616. With the embodiment of the filter device in FIGS. 8C-E, the proximal and distal filters are deployed using the corewire to actuate the deployment. To collapse the filters, the proximal filter is collapsed using the corewire while the distal filter is collapsed mechanically, for example, using a catheter or sheath to push against the lower struts. In this way, the two filters can be sequentially collapsed using a device with a single corewire.

For embodiments in which filter device 608 comprises filter elements that can be sequentially or independently actuated between a deployed configuration and a recovery configuration, proximal filter element 610 and/or distal filter element 612 can be placed into a recovery configuration under aspiration. In particular, an aspiration catheter can be introduced over guide structure 614 to a location proximal to proximal filter element 610 and, subsequently, proximal filter element 610 can be placed into a recovery configuration. The aspiration catheter can then be placed at a location proximal to distal filter element 612. Subsequently, distal filter element 612 can be place into a recovery configuration and protection device 608 can be removed with or without aspiration.

3. A Single Filter Structure to Span Arteries Along the Aortic Arch

A method for providing embolic protection during a heart procedure can comprise deployment and recovery of a protection system comprising a single filter structure that spans along the aortic arch. More specifically, a method for providing embolic protection with these embodiments of a filtration system comprises deploying a portion of the filter structure within the brachiocephalic artery and a portion of the filter structure within the left carotid artery. Generally, the filter structure is tracked through the right subclavian artery through to the left carotid artery. The filter structure is deployed with the filter in the desired location. The filter can comprise elements that are self expanding or elements that are actuated for deployment. In any case, the deployed filter element generally has elements that at least approximately seal with the carotid artery and the brachiocephalic artery such that flow from the aorta is filtered into these arteries.

Furthermore, the method of using these filter devices further comprises recovery of the filter structure. Generally, recovery of a filter structure comprises placing the filter structure in a recovery configuration and removing the filter structure from a patient's body. Placing a filter structure and/or removing the filter structure from a patient can be done with or without aspiration.

With the filtration system illustrated in FIG. 10, a method for embolic protection comprises deployment and recovery filter structure 510. A method for deploying filter structure 510 can comprise delivery of catheter 508 through the right subclavian artery and into the left carotid artery. The deployment method further comprises delivery of the filter structure 520 through a central lumen 518 through catheter 508. Filter structure 520 can be preloaded within catheter 508, or filter structure 520 can be tracked through catheter 508 following placement of catheter 508 within the vessel. In some embodiments, filter structure 520 can be placed within catheter 508 for delivery so that distal hoop 522 and proximal hoop 520 is located within catheter 522 in a lower profile configuration. Subsequently, the deployment comprises moving catheter 508 proximally relative to filter structure 510 so that distal hoop 522 extends completely from catheter 508 and within the left common carotid artery. Catheter 508 is further moved proximally to filter structure 510 so that a filter element 512 extends completely from catheter 508 and so that proximal hoop 520 is located within the brachiocephalic artery. Proximal hoop 520 and distal hoop 522 can be self deploying such that these hoops assume an extended configuration forming a seal with the vessel walls upon release in the vessel. Subsequently, catheter 508 can be partially withdrawn, completely withdrawn, or left in place.

Recovery of filter structure 510 can comprise moving catheter 508 distally along tethers 514, 516 and over filter structure 510 so that filter structure 510 is completely contained within catheter 508. Proximal hoop 520 and distal hoop 522 can be formed of a resilient material such that mechanical forces distort the hoops for recovery into catheter 508. In some embodiments, tethers 514, 516 can be used to pull filter element 510 in a deployed configuration to displace emboli on the surface of such that the emboli flow down the descending aorta into vessel in which the emboli would not generally cause any significant adverse effects. If these emboli flow down the descending aorta, the emboli are not present to flow into the carotid arteries, where the emboli can cause significant adverse events. After filter structure 510 is withdrawn into catheter 508, filter structure 510 can be removed through catheter 508 or filter can be removed simultaneously with catheter 508. In other embodiments of the recovery method, an aspiration catheter can be substituted for catheter 508.

With respect to the filter system in FIG. 11A, catheter/tubular element 544 is tracked through the right subclavian artery such that the distal tip is within the left carotid artery. When tubular element is in position, occlusive elements 546, 458 are deployed to form seals against the vessel walls. With the design shown in FIG. 11A, occlusive elements 546, 548 are simultaneously deployed, although in alternative embodiments, it may be possible to sequentially deploy occlusive elements 546, 548, such as if there are separate inflation lumens. Once occlusive elements 546, 548 are deployed flow from the aorta into the carotid arteries is filters. To remove the filter system from the patient, occlusive elements 546, 548 are deflated or otherwise transitioned to a recovery configuration unsealed from the vessel walls. Then, the filter device can be removed from the vessel. The placement of the filter elements within tubular element 544 protects the filters to reduce the change that emboli become displaced during removal of the filter device.

4. Catheter With an Exterior Filter to Filter Flow in the Aorta

With respect to the deployment of filters within the ascending aorta on the exterior of a catheter, the catheter can be tracked into position prior to the commencement of the procedure on the heart. Generally, the catheter is delivered into the ascending aorta with the filter element, such as filter 584 of FIG. 12, in a low profile delivery configuration. Once in position, the filter element can be deployed into an extended configuration. Desired devices for the heart procedure can be tracked through the catheter. After completion of the procedures that create a risk of emboli generation, the filter element can be transitioned to a recovery configuration, and the catheter with the collapsed filter element can be removed. The recovery of the catheter and filter element can be assisted with an aspiration catheter.

Distribution And Packaging

The medical devices described herein are generally packaged in sterile containers for distribution to medical professionals for use. The articles can be sterilized using various approaches, such as electron beam irradiation, gamma irradiation, ultraviolet irradiation, chemical sterilization, and/or the use of sterile manufacturing and packaging procedures. The articles can be labeled, for example with an appropriate date through which the article is expected to remain in fully functional condition. The components can be packaged individually or together.

Various devices described herein can be packaged together in a kit for convenience. The kit can further include, for example, labeling with instruction for use and/or warnings, such as information specified for inclusion by the Food and Drug administration. Such labeling can be on the outside of the package and/or on separate paper within the package.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

We claim:

1. A filtration system comprising:
a catheter comprising a tubular element having a proximal end and a distal end, an occlusive element mounted toward the distal end on the exterior of the tubular element, a lumen extending through the tubular element with a distal opening, a first filter element at a securely fixed position proximal to the distal opening, an open portion of the tubular element proximal to the occlusive element near the distal end in fluid communication with the first filter element, wherein the first filter element is configured to filter flow entering the lumen at the distal opening as unfiltered flow before the flow exits the catheter through the open portion of the tubular element; and
a filter device comprising a guide structure and a second filter element distinct from the first filter element mounted on the guide structure,
wherein the guide structure extends within the lumen of the catheter, which is configured for the delivery of the second filter element mounted on the guide structure.

2. The filtration system of claim 1, wherein a distance between the occlusive element and the second filter element can be extended to span the aortic arch between aortic entrances of the brachiocephalic artery and the left carotid artery of a human patient.

3. The filtration system of claim 1, wherein the occlusive element comprises a balloon.

4. The filtration system of claim 3, wherein the balloon in a deployed configuration has a diameter large enough to occlude a brachiocephalic artery.

5. The filtration system of claim 3, wherein the balloon is made out of a compliant deformable material.

6. The filtration system of claim 3, wherein the tubular element of the catheter further comprises a balloon inflation lumen in fluid communication with the balloon.

7. The filtration system of claim 1, wherein the first filter element comprises fibers.

8. The filtration system of claim 7, wherein at least some of the fibers are surface capillary fibers.

9. The filtration system of claim 7, wherein at least some of the fibers comprise polymer.

10. The filtration system of claim 1, wherein the first filter element comprises a porous membrane.

11. The filtration system of claim 1, wherein the second filter element comprises surface capillary fibers having a first configuration in a bundle with a low profile and an extended configuration with centers of the fibers flaring outward from the guide structure, wherein the guide structure comprises a corewire and an overtube with the corewire extending through a lumen of the overtube, and wherein the relative movement of the corewire and the overtube transitions the fibers from the low profile configuration to the extended configuration.

12. The filtration system of claim 1, wherein the second filter element comprises a filter basket.

13. The filtration system of claim 12, wherein the filter basket comprises an opening into the filter basket oriented toward the proximal end of the filtrations system.

14. The filtration system of claim 1, wherein a diameter of the tubular member is suitable for placement inside aortic arch percutaneously.

15. A method for providing embolic protection during an endovascular procedure on a patient's heart using a filtration system comprising a catheter comprising a tubular element having a proximal end and a distal end, an occlusive element mounted toward the distal end on the exterior of the tubular element, a lumen extending through the tubular element with a distal opening, a first filter element proximal to said distal opening, an open portion of the tubular element proximal to the occlusive element near the distal end in fluid communication with the first filter element, wherein the first filter element is configured to filter flow entering the lumen at the distal opening as unfiltered flow before the flow exits the catheter through the open portion of the tubular element; and a filter device comprising a guide structure and a second filter element distinct from the first filter element mounted on the guide structure, wherein the lumen of the catheter is suitable for the delivery of the second filter element mounted on the guide structure, the method comprising, delivering the catheter through a right sub-clavian artery to position the occlusive element close to an aortic entrance of a brachiocephalic artery, delivering the second filter element through the lumen of the catheter into a left carotid artery, and deploying the occlusive element and the second filter element to filter blood flow into a right carotid artery through the first filter element and into the left carotid artery through the second filter element.

16. The method of claim 15, wherein the occlusive element is a balloon and the method further comprising deploying the balloon to occlude direct blood flow into the right carotid artery while allowing blood flow to enter the lumen of the catheter to go through the first filter element so that filtered blood can flow into the right carotid artery, by passing the balloon.

17. The method of claim 15, further comprising performing an endovascular procedure on the heart, delivering a heart valve delivery catheter through a descending aorta or a sub-clavian artery to the heart to effect at least a step related to removal of a heart valve or the placement of a prosthetic heart valve, or performing a surgical procedure on the heart while the filtration system is filtering flow into the carotid arteries.

18. The method of claim 15, wherein the procedure comprises replacement of an aortic valve.

19. The method of claim 15, further comprising removing the filtration system from the arteries following performance of an endovascular procedure on the heart.

20. The method of claim 19, wherein at least a part of the removal process is accompanied by aspiration.

* * * * *